United States Patent [19]
Sellers et al.

[11] Patent Number: 6,124,282
[45] Date of Patent: Sep. 26, 2000

[54] DRUG FORMULATIONS

[76] Inventors: Edward M. Sellers, 78 Baby Point Cres., Toronto, Ontario, Canada, M6S 2C1; Rachel F. Tyndale, Apt. 5, 28 Brunswick Ave., Toronto, Ont, Canada, M5S 2L7

[21] Appl. No.: 09/083,027

[22] Filed: May 22, 1998

Related U.S. Application Data

[60] Provisional application No. 60/041,500, May 22, 1997.

[51] Int. Cl.[7] .......................... A61K 31/44; A61K 31/54
[52] U.S. Cl. ...................... 514/227.5; 514/284; 514/357
[58] Field of Search ................................ 514/227.5, 284, 514/357

[56] References Cited

U.S. PATENT DOCUMENTS

| | | | |
|---|---|---|---|
| 5,166,207 | 11/1992 | Smith | 514/270 |
| 5,932,589 | 8/1999 | Angeli | 514/289 |

OTHER PUBLICATIONS

Derwent Abstract of WPIDS 66–27387F, 1993.
Benowitz NL, et al., *Pharmacogenetics* 6,239–242, 1996.
Broly F, et al., *DNA Cell Biol* 1991:10, 545–558, 1991.
Busto, U.E., et al., *Clin. Pharmacol. Ther.* 55:451–463, 1994.
Caraco, Y., et al., *J. Pharmacol. Exp. Ther.* 281(1): 330–336, 1997.
Cone, E.J., et al., *Drug Metab. Dispos.* 6: 488–493, 1978.
Davis H, et al., *Int J Addict* 26, 777–795, 1991.
Dayer, P., et al., *Biochem. Biophys. Res. Commun.* 152:411–416, 1988.
Di Chiara, et al., Trends Pharmacol. Sci. 13: 185–193, 1992.
Fischman, M.W., et al., Br. J. Addict. 86: 1563–1570, 1991.
Heim, M.H., et al., *Genomics* 1002: 14, 49–58.
Herheimer A. *Drug and Therapeutics Bulletin* 23(16):62–64, 1985.
Holtzman S.G., J. Pharmacol. Exp. Ther. 214:614–9, 1980.
Isaac, P., et al., Can. J. Clin. Pharmacol. 2(2):81–86, 1995.
Jacqz–Agrain E., et al., Pharmacogenetics 3:197–204, 1993.
Jasinski, D.R.: Assessment of the abuse potential of morphine–like drugs (methods used in man). In Handbook of Experimental Pharmacology, vol. 45/I. Drug Addiction I: Morphine, Sedative Hypnotic and Alcohol Dependence. Ed. by: W.R. Martin, pp. 197–258, Springer–Verlag, Heidelberg, 1977.

Jensen, S. et al., Int. J. Leg. Med. 105:279–293, 1993.
Kaplan, H.L., et al., J. Pharmacol. Exp. Ther. in press.
Kathiramalainathan, K., Kaplan, H.L., Busto, U.E., Romach, M.K., Tyndale, R.F., Sellers, E.M. Abstracts of XIth International Symposium on Microsomes and Drug Oxidations (Los Angeles, California), 239, 1996.
Kauppila T., et al., Pharmacol. Biochem. Behav. 52:641–4, 1995.
Koyuncuoglu H., et al., *Int. J. Clin. Pharmacol. Ther. Toxicol.* 28:147–52, 1990.
Kroemer, H.K., et al., *Life. Sci.* 56(26): 2285–2298, 1995.
Mortimer, O., et al., *Clin. Pharmaco.l Ther.* 47: 27–35, 1990.
O'Brien, C.P. Drug addiction and drug abuse. In: Hardman J, Limbird L, eds. Goodman and Gilman's The Pharmacological Basis of Therapeutics. 9th edition. Toronto: MacGraw–Hill, 1996: 557–577.
O'Conner LE, et al., *Inter J Addict* 1995: 30, 541–555, 1995.
Otton SV, et al., *Clin Pharmacol Ther* 54, 463–472, 1993a, 53, 401–409, 1993b.
Pollack, B., *Drug Info. J.* 30:669–74, 1996.
Romach, M.K., et al., U.E., Am. J. Psychiatry, 1997 (submitted).
Shadel, M., et al., et al., *J. Clin. Psycopharmacol* 15(5):263–269, 1995.
Tyndale, R.F., et al., *Pharmacogenetics* 1997, 7:375–379, 1997.
Wu, D., et al., *Br. J. Clin. Pharmac.* 35: 30–34, 1993.
Wu D, Otton SV, Inaba T, Kalow W, Sellers EM. Interactions of amphetamine analogs with human liver CYP2D6. *Biochem Pharmacol* 1996 (in press).
Zawertailo, L.A., et al., *J. Clin. Psychopharmacology* 15(2): 117–124, 1995.

*Primary Examiner*—Zohreh Fay
*Attorney, Agent, or Firm*—Bereskin & Parr

[57] ABSTRACT

Various compounds that can inhibit the enzyme CYP2D6 are disclosed. The compounds are useful in increasing the effectiveness and reducing the abuse potential of drugs that are metabolised by CYP2D6.

12 Claims, 16 Drawing Sheets

The metabolic pathways of dextromethorphan in humans.

Rate is expressed as the rate of DOR formed in nmole/mg protein/min.

[Substrate] is expressed as DEM concentration in μM.

Km = 6.0 μM

Vmax = 0.60 nmoles/mg protein/min

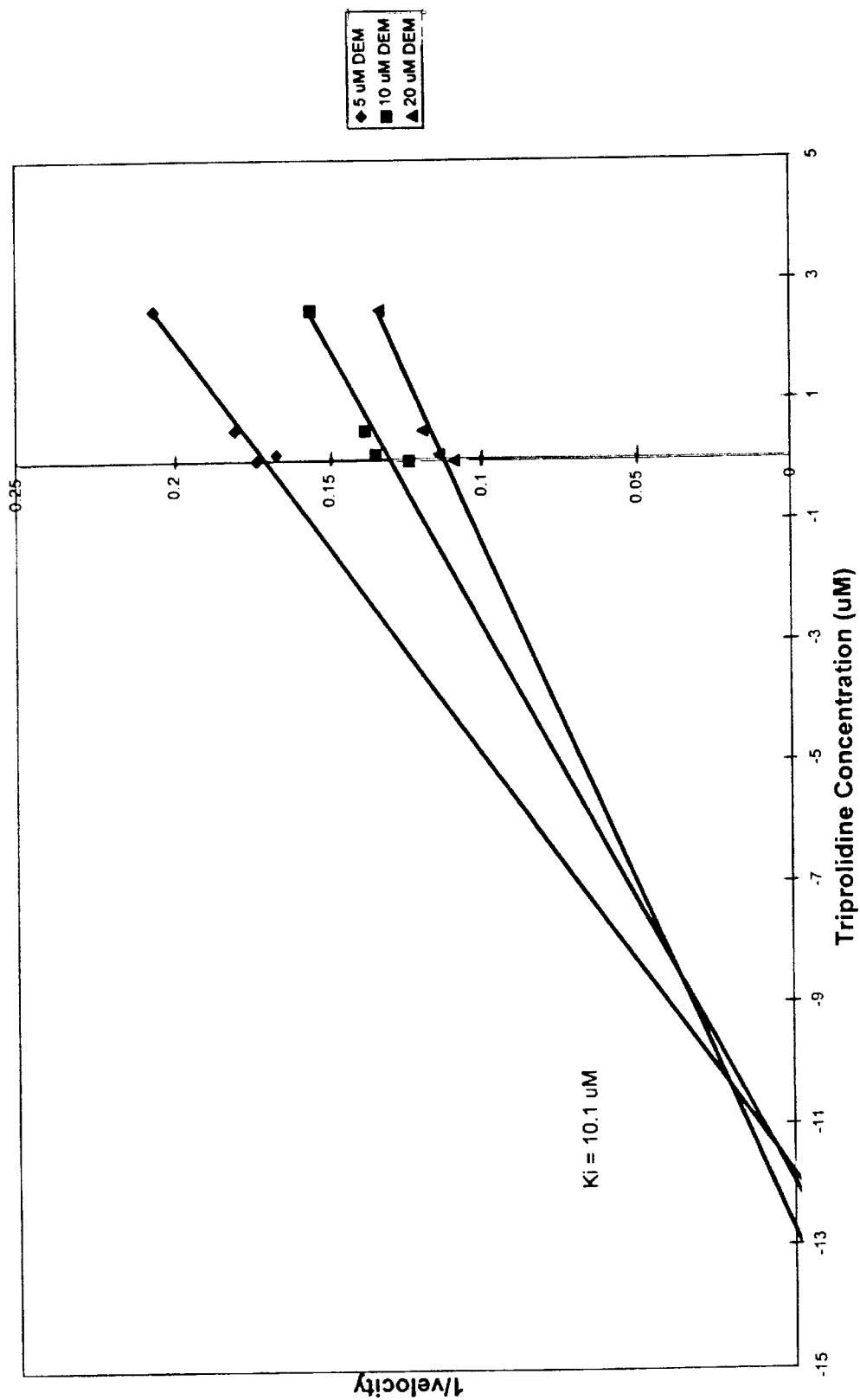

DRUG FORMULATIONS

This application claims benefit from U.S. Provisional Application, Ser. No. 60/041,500 filed May 22, 1997 which is incorporated herein by reference in its entirety.

FIELD OF THE INVENTION

The invention relates to improved drug formulations that are long lasting and have a decreased abuse potential.

BACKGROUND OF THE INVENTION

The cytochrome P450 (CYP) system has been implicated in the metabolism of many drugs including dextromethorphan, codeine, hydrocodone, amphetamine, oxycodone and methamphetamine. These drugs have various pharmacological effects including analgesia, sedation and antussive effects (or the suppression of cough).

One of these, codeine, is an opioid drug that is widely used for pain relief (analgesia) and for cough suppression (anti-tussive). While most codeine use appears to be for medical purposes, there is increasing evidence that some individuals use this drug non-medically for its mood-altering properties (Jensen and Hansen, 1993; Isaac et al., 1995; Romach et al.).

The metabolism of codeine follows three major pathways: conjugation to codeine-6-glucuronide; N-demethylation to norcodeine; and O-demethylation to morphine. The conjugation pathway is quantitatively the most important, with codeine-6-glucuronide recovered in urine accounting for 70% of an oral dose of codeine. The corresponding values for N-demethylation and O-demethylation are approximately 7% and 5% respectively. About 4% is excreted unchanged (Yue et al., 1991). The O-demethylation pathway, although quantitatively small, is of pharmacological importance because morphine and some of its metabolites (morphine-6-glucuronide and normorphine) are pharmacologically more potent than codeine or any of its non-O-demethylated metabolites. The O-demethylation of codeine to morphine is catalyzed by the genetically polymorphic drug metabolizing enzyme cytochrome 2D6 (CYP2D6) (Dayer et al., 1988; Mortimer et al., 1990).

CYP2D6 is absent in approximately 7% of the Caucasian population due to the homozygous expression of inactivating mutations in the CYP2D6 gene (reviewed by Kroemer and Eichelbaum, 1995). Such individuals are referred to as 'poor metabolisers' (PMs), while those who express functional CYP2 D6 enzymes are 'extensive metabolisers' (EMs).

Previous studies have addressed the importance of metabolic O-demethylation to the analgesia, respiratory depression and decreased gastrointestinal motility of codeine (Sindrup et al., 1990; 1992; Desmeules et al., 1991; Caraco et al., 1996; Poulsen et al., 1996). Codeine analgesia was shown to be impaired in PMs as well as in EMs who had been temporarily converted to PMs through pretreatment with the potent and selective CYP2 D6 inhibitor quinidine (Sindrup et al., 1990, 1992). Diminished production of morphine in extensive metabolizers of codeine after quinidine was associated with significantly reduced respiratory, psychomoter and pupillary effects (Caraco et al., 1996). Increasing codeine's N-demethylation by rifampin treatment is associated with attenuation of codeine's respiratory and psychomoter effects in EMs but not CYP2 D6 deficient PMs (Caraco et al., 1997). The results of these studies therefore imply a substantial contribution by the O-demethylated metabolites to the pharmacologic properties of codeine. With respect to abuse and dependence potential however, the roles of parent drug and metabolites are largely unknown.

The pain-relieving properties of opioids are mediated by $\mu$ opioid receptors (Székely, 1994). The O-demethylated metabolites of codeine have a substantially greater affinity for the $\mu$ receptor than do codeine or any of the non-O-demethylated metabolites, and this is the basis for their postulated importance in codeine analgesia (Sindrup and Brosen, 1995). For example, the affinity of morphine for the $\mu$ opiate receptors in 200-fold greater than that of codeine; the affinity of morphine-6-glucuronide, a metabolite of morphine, is 400-fold greater than that of codeine; and the affinity of normorphine, another morphine metabolite, is 50-fold greater than that of codeine (Chen et al., 1991). The subjective effects of opioid agonists considered important for abuse liability (such as subjective elation, euphoria, "liking", etc.) are also mediated through the $\mu$ receptors (Székely, 1994; Di Chiara and North, 1992).

Another drug that is present in cough formulations is dextromethorphan (DEX). DEX is a methylated dextrorotatary analog of levorphanol (a morphine analog) (Bern and Peck, 1992), but it does not possess the full range of central nervous system effects common to opioid agonists (Tortella et al., 1989). The drug has been widely used for its antitussive properties for many years and is available as an over-the-counter preparation in most countries, including Canada and the United States. DEX has also been investigated as a possible pharmacotherapy for a variety of neurodegenerative disorders such as amyotrophic lateral sclerosis, (Hollander, 1994; Blin, 1996) idiopathic Parkinson disease, (Saenz, 1993; Montastruc, 1994) and Huntington disease (Walker, 1989). Experimental studies have investigated the analgesic properties of DEX in humans (Kauppila, 1995) and its use as possible pharmacotherapy for heroin addiction (Koyuncuoglu and Sadam, 1990). Dextromethorphan, or DEX, has been used in the USA for about 30 years and a large body of clinical experience has been used to formulate a safety profile for DEX. An anthology of adverse drug events has been analyzed, drawn both from published case records and a data base recording DEX-related adverse events spontaneously reported by physicians or pharmacists (Bern and Peck, Dextromethorphan. An overview of safety issues. Drug Safety. 7(3):190-9. 1992). The resulting safety profile indicates that adverse drug reactions are infrequent and usually not severe. The predominate symptoms are usually dose related and include neurological, cardiovascular and gastrointestinal disturbances. Particular safety concerns arise when monoamine oxidase inhibiting (MAOI) drugs and DEX are coadministered. In addition to adverse drug reactions, the safety profile of DEX is affected by episodic and sporadic abuse. In fact, abuse appeared to be the most significant hazard identified by analysis of spontaneous adverse event reporting. No evidence could be found that the well documented pharmacokinetic polymorphism observed with dextromethorphan is correlated with any clinically significant safety risk if it is used for short term treatment. In summary, the safety profile of dextromethorphan is reassuring, particularly relating to overdose in adults and children.

Dextrorphan (DOR) is a metabolite of dextromethorphan, being produced when DEX is metabolized by the liver enzyme cytochrome P4502D6 or CYP2 D6 (debrisoquine 4-hydroxylase). Conversion involves the removal of a methyl group (CII3) at position 6. This removal is termed "O-demethylation" and is the major route of removal of DEX from the body. Between 5 to 10% of the Caucasian population lack this enzyme, and in the remaining population the rate of metabolism (activity of this enzyme) can vary tremendously.

DOR is very similar chemically to DEX, but reacts with different receptors in the body, and shows a different affinity, or spectrum of affinities and subsequent actions for those receptors with which DEX also reacts. DOR is an active metabolite with anticonvulsant, sedative, and antitussive properties and an affinity for the phencyclidine (PCP) site of the ligand-gated channel of the N-methyl D-aspartate (NMDA) receptor complex ($K_1$=222 nM) (Wong, 1988). The affinity of DOR is similar to that of ketamine ($D_1$=200 nM) (Parsons, 1995) and is much higher than that of the parent drug, DEX; $K_1$=3500 nM (Newman, 1996). However, the binding affinity of DOR for the NMDA receptor complex is not as high as that of PCP ($K_1$=42 nM) (Wong et al., 1988), a prototypic NMDA antagonist (Hampton, 1982) and a well-known drug of abuse (Stillman, 1979). However, it is believed that DOR is principally responsible for the abuse potential of the parent drug dextromethorphan. Cough suppression can be mediated exclusively by the parent drug, DEX, and occurs in the absence of conversion to DOR, i.e., no metabolism is required for antitussive efficacy.

Hydrocodone is also used as an antitussive, analgesic and sedative medication and it too undergoes the same routes of metabolism as DEX and codeine: Hydrocodone is metabolised to hydromorphone, which has a higher abuse potential than the parent compound. As such, as for DEX and codeine, the metabolities appear to contribute to the abuse potential of the parent drug, however, the roles of parent drug and metabolite(s) are largely unknown.

In view of the abuse potential of drugs found in cough formulations (such as dextromethorphan, codeine and hydrocordone) there is a need for improved cold or cough formulation that have a reduced abuse potential but long lasting therapeutic effect.

SUMMARY OF THE INVENTION

The inventors have surprisingly found that several drugs that are normally used to treat colds or cough, including antihistamines and antitussive agents can inhibit the enzyme CYP2 D6. In particular, the inventors have shown that the antihistamines, pyrilamine, phenyltoloxamine, brompheniramine, promethazine, doxylamine, diphenhydramine, triprolodine, and chlorpheniramine and the antitussive agent, glaucine, inhibit the activity of CYP2 D6. Accordingly, the present invention provides a method for inhibiting the enzyme CYP2 D6 comprising administering an effective amount of at least one CYP2 D6 inhibitor selected from the group consisting of pyrilamine, phenyltoloxamine, brompheniramine, triprolodine, promethazine, doxylamine, diphenhydramine chlorpheniramine, and glaucine to an animal in need thereof. Preferably, the inhibitor is glaucine.

The above-mentioned drugs are useful in inhibiting the metabolism of any drug that is metabolized by the enzyme CYP2 D6. Accordingly, the present invention provides a method for inhibiting the metabolism of a drug that is metabolized by the enzyme CYP2 D6 comprising administering an effective amount of at least one CYP2 D6 inhibitor selected from the group consisting of glaucine, brompheniramine, promethazine pyrilamine, doxylamine, diphenhydramine phenyltoloxamine, triprolodine and chlorpheniramine.

The CYP2 D6 inhibitors of the invention can be used to increase the effectiveness and/or decrease the abuse liability of certain drugs that are metabolised by CYP2 D6. In a preferred embodiment, the CYP2 D6 inhibitors of the invention are used to inhibit the metabolism of drugs that are present in cough medications such as dextromethorphan and codeine.

The present invention also includes pharmaceutical compositions containing the CYP2 D6 inhibitors of the invention. In a preferred embodiment, the present invention provides an improved composition for the treatment of cough or colds comprising: (1) a drug that is effective in treating coughs or colds, and (2) a CYP2 D6 inhibitor that inhibits the metabolism of the first drug selected from the group consisting of glaucine, brompheniramine, promethazine pyrilamine, doxylamine, diphenhydramine phenyltoloxamine, tripolodine and chlorpheniramine. The first drug is preferably dextromethorphan or codeine.

In a preferred embodiment, the invention provides a long-lasting cough formulation comprising: (i) dextromethorphan and/or codeine, and (ii) glaucine.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 7A is a graph showing Dixon plot of triprolidine inhibition of DEM to DOR formation in K20 human liver microsome.

DETAILED DESCRIPTION OF THE INVENTION

1. Methods of the Invention

Figure 1:
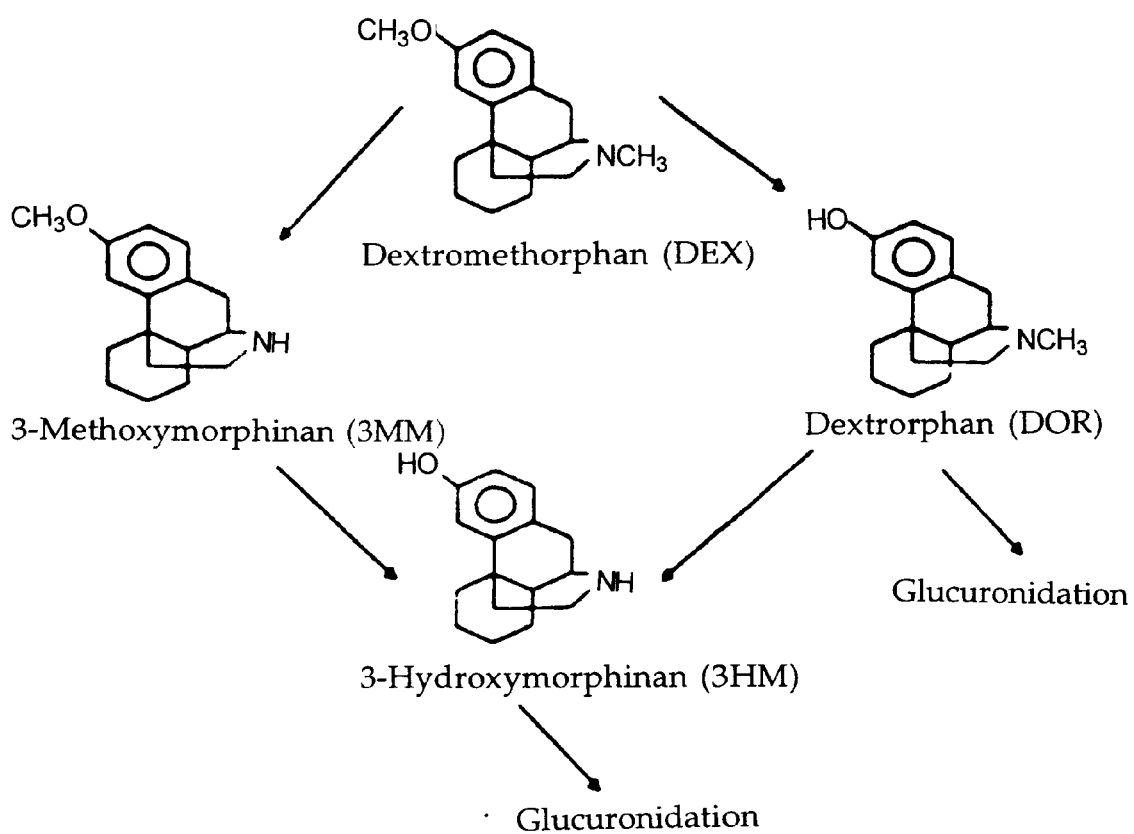
FIG. 1 shows the metabolic pathway of dextromethorphan in humans.

As hereinbefore mentioned, the present inventors have surprisingly found that several antihistamines and antitussive agents can inhibit the enzyme CYP2D6. In particular, the inventors have shown that the antihistamines, pyrilamine, phenyltoloxamine, brompheniramine, triprolodine, and chloropheniramine and the antitussive agent, glaucine, inhibit the activity of the enzyme CYP2D6. Accordingly, the present invention provides a method for inhibiting the enzyme CYP2D6 comprising administering an effective amount of at least one CYP2D6 inhibitor selected from the group consisting of pyrilamine, phenyltoloxamine, brompheniramine, triprolodine, promethazine, doxylamine, diphenhydramine chloropheniramine, and glaucine to an animal in need thereof.

The term "effective amount" as used herein means an amount effective and at dosages and for periods of time necessary to achieve the desired result. The term "animal" means any member of the animal kingdom including all mammals, preferably humans.

The drugs pyrilamine, phenyltoloxamine, brompheniramine, triprolodine, promethazine, doxylamine, diphenhydramine chloropheniramine, and glaucine may be collectively referred to herein as "the CYP2D6 inhibitors of the invention". The invention includes all forms of the CYP2D6 inhibitors of the invention including analogs, isomers and pharmaceutically acceptable salts thereof.

The method can be used to treat any condition wherein it is desirable to inhibit or suppress CYP2D6 activity.

The CYP2D6 inhibitors of the invention are useful in inhibiting the metabolism of any drug that is metabolized by the enzyme CYP2D6. Accordingly, the present invention provides a method for inhibiting the metabolism of a drug that is metabolized by the enzyme CYP2D6 comprising administering an effective amount of at least one CYP2D6 inhibitor selected from the group consisting of glaucine, brompheniramine, promethazine, pyrilamine, doxylamine, diphenhydramine diphenhydramine phenyltoloxamine, triprolodine and chloropheniramine to an animal in need thereof. The CYP2D6 inhibitors of the present invention can be used to inhibit the metabolism of many drugs as CYP2D6 metabolizes over 40 clinically used drugs (Heim & Meyer, 1992; Alvan et al., 1990). Examples of drugs that are metabolised by CYP2D6 include dextromethorphan, codeine, hydrocodone, neuroleptics such as chlorpromazine, fluphenazine, and paroxetine, and beta perphenazine and risperidone, antidepressants such as imipramine, desipramine, northriptyline, clomipramine and paroxetine, and beta blockers including some antiarrhythmic agents and some oncolytic agents (Pollock B., 1996).

In many drugs it is the parent drug that exerts the pharmacological effects. Therefore inhibiting the metabolism of the parent drug can increase the effectiveness of the drug by prolonging the life of the parent drug in the bloodstream. Accordingly, the present invention provides a method of increasing the effectiveness of a drug that is metabolised by CYP2D6 comprising administering an effective amount of the drug and an inhibitor of CYP2D6 selected from the group consisting of glaucine, brompheniramine, promethazine, pyrilamine, doxylamine, diphenhydramine diphenhydramine phenyltoloxamine, triprolodine and chloropheniramine to an animal in need thereof.

Standard assays may be used to determine if a CYP2D6 inhibiting compound of the invention inhibits the metabolism of a given drug. For example, the test drug can be incubated with the enzyme CYP2D6 in the presence and absence of a CYP2D6 inhibiting drug and it can be determined if the CYP2D6 inhibiting drug has any effect on the metabolism of the test drug.

In addition to increasing the effectiveness of certain drugs, the CYP2D6 inhibiting drugs of the invention can be used to decrease the abuse potential of certain drugs that are metabolised by CYP2D6. With some drugs that may be abused, it has been reported that it is the metabolite and not the parent drug that contributes to the abuse of the drug. For example, dextromethorphan(DEX) is metabolised to dextrorphan(DOR) by CYP2D6 via the pathway shown in FIG. 1. DOR has been reported to produce PCP-like behavorial effects in animals while DEX does not exhibit the same effects (Schadel et al. 1995). The inventors have administered a CYP2D6 inhibitor and DEX to eight human subjects and have demonstrated that the subjects experienced less euphoria and liking and could not tolerate as high a dose of DEX and experienced more side effects than the subjects that did not take the inhibitor. Overall, the inventors have demonstrated that DEX has a lower abuse potential when given with a CYP2D6 inhibitor.

Many opioids, such as codeine, are widely abused. Codeine is metabolised by CYP2D6 to morphine. The present inventors have shown that individuals who are poor metabolizers (PMs) of codeine are protected against the development of oral opiate dependence. In addition, they have shown that inhibiting the enzyme CYP2D6 converts extensive metabolizers (EMs) into PMs and significantly decreases codeine consumption. (Tyndale et al., 1997, incorporated herein by reference). Therefore, the CYP2D6 inhibitors of the invention may be useful in reducing the abuse and dependence on drugs that are metabolized by CYP2D6.

Accordingly, the present invention provides a method of decreasing the abuse potential of a drug that is metabolised by CYP2D6 comprising administering an effective amount of an inhibitor of CYP2D6 selected from the group consisting of glaucine, brompheniramine, promethazine, pyrilamine, doxylamine, diphenhydramine diphenhydramine phenyltoloxamine, triprolodine and chloropheniramine to an animal in need thereof.

In order to determine whether a CYP2D6 inhibiting drug of the invention affects the abuse potential of a drug one can use known methods for assaying abuse liability for example as described in Fischman and Foltinz (1991) or in applicant's priority application No. 60/041,500 which is incorporated herein in its entirety.

In a preferred embodiment, the CYP2D6 inhibitors of the invention are used to inhibit the metabolism of drugs that are present in cough medications such as dextromethorphan and codeine. Accordingly, the present invention provides a method of increasing the effectivness of a cough medication comprising administering an effective amount of an inhibitor of CYP2D6 selected from the group consisting of glaucine, brompheniramine, promethazine, pyrilamine, doxylamine, diphenhydramine diphenhydramine phenyltoloxamine, triprolodine and chlorpheniramine to an animal in need thereof. In a more preferred embodiment, the present invention provides a method of increasing the effectiveness of dextromethorphan or codeine comprising administering an effective amount of an inhibitor of CYP2D6 selected from the group consisting of glaucine, brompheniramine, promethazine, pyrilamine, doxylamine, diphenhydramine diphenhydramine phenyltoloxamine, triprolodine and chloropheniramine to an animal in need thereof.

2. Compositions

The CYP2D6 inhibitors of the invention can be formulated into pharmaceutical compositions for use in the methods described above. In one embodiment, the present invention provides a composition for inhibiting the enzyme CYP2D6 comprising an effective amount of at least one CYP2D6 inhibitor selected from the group consisting of pyrilamine, phenyltoloxamine, brompheniramine, triprolodine, promethazine, doxylamine, diphenhydramine, chloropheniramine, and glaucine in a pharmaceutically acceptable diluent or carrier. Preferably, the composition contains glaucine.

In another embodiment the present invention provides a long lasting and reduced abuse potential composition comprising (a) a drug that is metabolized by the enzyme CYP2D6, and (b) a CYP2D6 inhibitor selected from the group consisting of pyrilamine, phenyltoloxamine, brompheniramine, triprolodine, promethazine, doxylamine, diphenhydramine, chloropheniramine, and glaucine.

In a preferred embodiment, the compositions of the present invention are used in the treatment of coughs or colds. Accordingly, the present invention provides an improved composition for the treatment of cough or colds comprising: (1) a drug that is effective in treating coughs or colds, and (2) a CYP2D6 inhibitor that inhibits the metabolism of the first drug and is selected from the group consisting of pyrilamine, phenyltoloxamine, brompheniramine, triprolodine, promethazine, doxylamine, diphenhydramine chloropheniramine, and glaucine. The first drug is preferably dextromethorphan or codeine.

In a preferred embodiment the invention provides a long-lasting cough composition comprising: (i) dextromethorphan and/or codeine, and (ii) glaucine.

The dosages of the above compositions can vary depending on many factors such as the pharmacodynamic characteristics of the particular substance, and its mode and route of administration; age, health, and weight of the individual recipient; nature and extent of symptoms, kind of concurrent treatment, frequency of treatment, and the effect desired. Dextromethorphan is generally present in cough formulations in an amount from about 20 mg/day to about 200 mg/day.

The compositions of the present invention preferably contain suitable pharmaceutical carriers or diluents. Suitable pharmaceutical carriers and methods of preparing pharmaceutical dosage forms are described in *Remington's Pharmaceutical Sciences*, Mack Publishing Company, a standard reference text in this field. Suitable pharmaceutical diluents, excipients, or carriers suitable selected with respect to the intended form of administration, that is, oral tablets, capsules, elixirs, syrups and the like, consistent with conventional pharmaceutical practices.

The compositions are preferably for oral delivery, more preferably in the form of a syrup, such as a cough syrup.

For oral administration in liquid form, the oral active substances can be combined with any oral, non-toxid, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like. Cough formulations generally include (in addition to the active ingredients) sorbitol, saccharose, citric acid, flavouring and water.

For oral administration in the form of a table or capsule, the active substances can be combined with an oral, non-toxic, pharmaceutically acceptable, inert carrier such as lactose, starch, sucrose, glucose, methyl, cellulose, magnesium stearate, dicalcium phosphate, calcium sulfate, mannitol, sorbitol and the like. Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase patient acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl- paraben, and chlorobutanol.

The CYP2D6 inhibitors of the invention may also be administered in the form of liposome delivery systems, such as small unilamellar vesicles, large unilamellar vesicles, and multilamelar vesicles. Liposomes can be formed from a variety of phospholipids, such as cholesterol, stearylamine, or phosphatidylcholines.

The CYP2D6 inhibitors of the invention may also be coupled with soluble polymers which are targetable drug carriers. Examples of such polymers include polyvinylpyrrolidone, pyran copolymer, polyhydroxypropyl-methacrylamide-phenol, polyhydroxyethylaspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

More than one CYP2D6 inhibitors of the invention may be used in a composition.

The combination of a CYP2D6 inhibitor and a CYP3A inhibitor are included within the scope of the invention. The inhibitors may be administered concurrently, separately or sequentially.

3. Screening Methods

The present invention also includes a method of screening for other substances that inhibit CYP2D6 comprising assaying for a substance which selectively: (i) inhibits the activity of the enzyme, or (ii) inhibits transcription and/or translation of the gene encoding the enzyme.

According to one embodiment, a method of screening for a substance that inhibits the metabolism of a drug comprises the steps of:

(a) reacting the drug in the presence of the test substance;

(b) assaying for one or more metabolites; and (c) comparing to controls to determine if the substance inhibits conversion.

In another embodiment, a method is provided for screening for a substance that inhibits the activity of CYP2D6 comprising the steps of:

(a) reacting a substrate of the CYP2D6 enzyme, in the presence of a test substance;

(b) assaying for any one or more of reaction product, unreacted substrate or unreacted CYP2D6; and (c) comparing to controls to determine if the test substance inhibits the CYP2D6 enzyme.

Substrates of CYP2D6 which may be used in the method of the invention for example include dextromethorphan, codeine and hydroccordone and analogs and derivatives thereof. The corresponding reaction products for dextromethorphan, codeine and hydrocordone are dextrorphan, morphine and hydromorphone, respectively.

The CYP2D6 enzyme used in the screening method of the invention may be obtained from natural, recombinant, or commercial sources.

Conditions which permit the formation of a reaction product may be selected having regard to factors such as the nature and amounts of the test substance and the substrate.

The reaction product, unreacted substrate, or unreacted enzyme such as CYP2D6; may be isolated by conventional isolation techniques, for example, salting out, chromatography, electrophoresis, gel filtration, fractionation, absorption, polyacrylamide gel electrophoresis, agglutination, or combinations thereof.

For example, to facilitate the assay of the reaction product, unreacted substrate, or unreacted enzyme; antibody against the reaction product or the substance, or a labelled enzyme or substrate, or a labelled substance may be utilized. Antibodies, enzyme, substrate, or the substance may be labelled with a detectable marker such as a radioactive label, antigens that are recognized by a specific labelled antibody, fluorescent compounds, other enzymes, antibodies specific for a labelled antigen, and chemiluminescent compounds.

The substrate enzyme or substance used in the method of the invention may be insolubilized. For example, it may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyaminemethyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized enzyme, substrate, or substance may be prepared by reacting the material with a suitable insoluble carrier using known chemical or physical methods, for example, cyanogen bromide coupling.

In another embodiment, a method is provided for screening for a substance that inhibits the metabolism of a drug to its potentially abusive metabolite by inhibiting transcription and/or translation of the gene encoding the CYP2D6 enzyme that catalyses the conversion.

Accordingly, the method of the invention comprises, under conditions such that the CYP2D6 enzyme that catalysts the metabolism of a drug is capable of being transcribed and/or translated, and providing the necessary elements for the transcription or translation of the nucleic acid sequence, and optionally a reporter gene, the steps of:

(a) culturing a host cell comprising a nucleic acid molecule containing a nucleic acid sequence encoding the enzyme and in the presence of a test substance; and (b) comparing the level of expression of the enzyme, or the expression of the protein encoded by the reporter gene, with a control cell transfected with a nucleic acid molecule containing a nucleic acid sequence encoding the enzyme in the absence of the test substance to determine if the test substance inhibits transcription and/or translation.

A host cell for use in the method of the invention may be prepared by transfecting a suitable host with a nucleic acid molecule comprising a nucleic acid sequence encoding the enzyme being assayed. A nucleic acid sequence encoding the enzyme may be constructed having regard to the sequence of the enzyme gene such as, for example, the human CYP2D6 sequence published in GenBank under accession number M33388, following procedures known in the art. Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements such as an origin of replication, additional DNA restriction sties, enhancers, and sequences conferring inducibility of transcription may be incorporated into the expression vector. It will also be appreciated that the necessary transcription and a translation elements may be supplied by the native enzyme's gene and/or its flanking sequences.

Examples of reporter genes are genes encoding a protein such as β-galactosidase, chloramphenicol acetyltransferase, firefly luciferase, or an immunoglobulin or portion thereof such as the Fc portion of an immunoglobulin, preferably IgG. Transcription of the reporter gene is monitored by changes in the concentration of the reporter protein such as β-galaciosidase, chloramphenicol acetyltransferase, or firefly luciferase. This makes it possible to visualize and assay for expression of the enzyme and in particular to determine the effect of a substance on expression of the enzyme.

Suitable host cells include a wide variety of prokaryotic and eukaryotic host cells, including bacterial, mammalian, yeast or other fungi, viral, plant, or insect cells.

Protocols for the transfection of host cells are well known in the art (see, Sambrook et al. Molecular Cloning A Laboratory Manual, 2nd edition, Cold Spring Harbor Laboratory Press, 1989, which is incorporated herein by reference).

Host cells which are commercially available may also be used in the method of the invention. For example, the h2A3 and h2B6 cell lines available form Gentest Corporation are suitable for the screening methods of the invention.

Also contemplated are kits containing the necessary reagents and materials and appropriate instructions to conduct the screening tests of the present invention.

The following non-limiting examples are illustrative of the present invention:

EXAMPLES

Example 1

Inhibition of CYP2D6

The inventors have tested a variety of antihistamines and the expectorant guaifenesin and the antitussive agent glaucine for their ability to inhibit the enzyme CYP2D6, by studying the metabolism of DEX to DOR. Microsomes from human livers were used to carry out these tests.

Materials and Methods

Preparation of Liver Microsomes

Human livers (K20, K25 and K27) from organ donors were donated by Dr. Inaba of the University of Toronto and they had been determined to be homozygous wild-type for the CYP2D6 polymorphism. The tissue was allowed to thaw at room temperature and then minced on ice. The liver was mixed with six volumes of cold isotonic KC1 (1.15%), homogenized and then centrifuged at 9000×g at 4° C. for 60 min. After which the supernatant was centrifuged at 100,000×g at 4° C. for 60 min. Next the pellet was re-suspended in cold isotonic KC1 to four times the original volume of the 9000 g supernatant. The specimen was then homogenized by hand and centrifuged at 100,000×g at 4° C. for 60 min. The pellet was resuspended in cold isotonic KC1 in 2 times the volume of the pellet to produce the washed microsomes. The liver microsomes were stored at −70° C. until use.

Screening of the effects of the drugs on CYP2D6 mediated DEX metabolism

The drugs which were screened for inhibitory activity included brompheniramine, chlorpheniramine, doxylamine, phenyltoloxamind, pheniramine, pyrilamine, diphenhydramine, triprolidine, and promethazine, which are all antihistamines, guaifenesin, which is an expectorant (Herheimer A. *Dug and Therapeutics Bulletin* 23(16):62–64 (1985)) and glaucine, which is an antitussive agent (Jaffe, J. H., Martin W. R., Goodman and Gilman's the Pharmacological Basis of Therapeutics (Gilman A. G., Nies A. S., Taylor P., 8th ed.), Pergamon Press, New York, pp. 485–521). The incubation mixture consisted of 75 $\mu$l of 0.2M potassium-phosphate buffer (pH 7.4), 50 $\mu$l of the drug being tested with final concentrations of 25 and 100 $\mu$M, 50 $\mu$l of human liver microsome with final concentration of 0.3 mg/ml, and 25 $\mu$l of NADPH with final concentration of 0.8 mM. The mixture was pre-incubated for 5 min at 37 C. and then 50 $\mu$l of DEM with final concentration of 5 $\mu$M, which was the approximate Km value, was added and incubated for at 37° C. for 30 min. Then 10 $\mu$l of 70% PCA was added to stop the reaction.

Ki determination of inhibitors

The incubation mixture consists of 75 $\mu$l of 0.2M potassium-phosphate buffer (pH 7.4), 50 $\mu$l of the drug being tested with final concentrations ranged from 0 to 100 $\mu$M, 50 $\mu$l of human liver microsome with final concentration of 0.15 mg/ml (since the stock of liver microsome was running out), and 25 $\mu$l of NADPH with final concentration of 0.8 mM. The mixture was pre-incubated for 5 min at 37° C. and then 50 $\mu$l of DEM with final concentration of 5, 10, or 20 $\mu$M, was added and incubated at 37° C. for 30 min. Then 10 $\mu$l of 70% perchloric acid PCA was added to stop the reaction.

Data Interpretation

The amount of the metabolite DOR formed in the incubation mixture was used as a measure of the activity of CYP2D6. The peaks of DOR, norfluroxetine and DEM were expected at retention times of 5.7, 10.5, 12.4 min., respectively. When some of the drugs being tested interfere with the peaks of DOR, an electrochemical detector was used instead in a similar way, but the metabolites was detected with different retention times. The area ratio of DOR to norfluroxetine in CYP2D6 was calculated to determine the relative amount of DEM present in the sample. In order to determine the concentrations of DOR present in the samples, the integrator was calibrated every time before injecting a new set of samples by a set of standard solutions with known concentrations of metabolites. In the CYP2D6 study, calibration curves were constructed over DOR concentration of 0.1, 0.5, 1.0, 5.0 nmole/100 $\mu$l of DOR. By comparing the area ration of DOR to norfluroxetine and DOR concentration is standard curve, the area ratio of the samples generated was converted to concentration in nmoles/ml.

Extraction Procedures

After incubation, 50 $\mu$l of 100 $\mu$l of 100 $\mu$M norfluroxetine was added to the samples in the CYP2D6 study, as an internal standard. The sample was then vortexed and centrifuged at 3000 rpm for 5 mon. 100 $\mu$l of the supernatant was pipetted into tubes and ready for high performance liquid chromatography (HPLC) analysis.

Liquid Chromatography

The HPLC system used was comprised of a Hewlett-Packard Model 1050 HPLC, and a 3396 Series II/9114B integratory (Hewlett Packard Co., Palo Alto, Calif.), a 15×0.46 mm, 5-$\mu$M phenyl column (Chromatography Sciences Co., Montreal, Canada), and a fluorescent detector (Applied Biosystems, Ramsey, N.J.) with the excitation and emission wavelengths of 195 and 280 nm respectively. When some of the drugs being tested interfered with the signal detected by the fluorescent detector, an ESA Coulochem II electrochemical detector was used as an alternative. The mobile phase was 10 mM monobasic potassium phosphate buffer containing acetonitrile:water (22:78, v/v) and 1 mM hepatensulfonic acid adjusted to pH 3.8 with orthophosphoric acid, and the flow rate was 1.5 ml/min.

30 $\mu$l of the supernatant of the incubation mixture in the injection vials were injected into the HPLC system. The levels of DEM and its metabolites present in the samples were detected based on their differences in the distribution in the mobile phase in the system and their different rates at which they travel and elute through the column.

Helium gas was pumped into the mobile phase to make sure that there is no air bubbles present in the column.

Results

Figure 2:
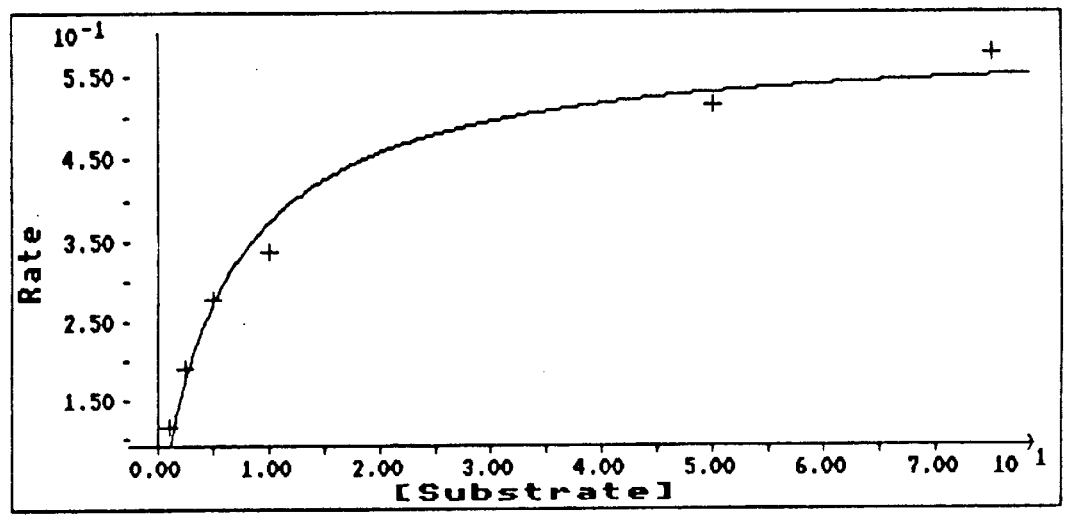
FIG 2 is a graph showing the kinetics of DEM to DOR formation in K20 human liver microsomes.

Km and Vmax of the CYP2D6 mediated DEM metabolism was determined to be 6.0 $\mu$M and 0.60 nmoles/mg protein/min respectively for a Caucasian human liver genotyped wt/wt (K20) shown in FIG. 2.

Figure 3:
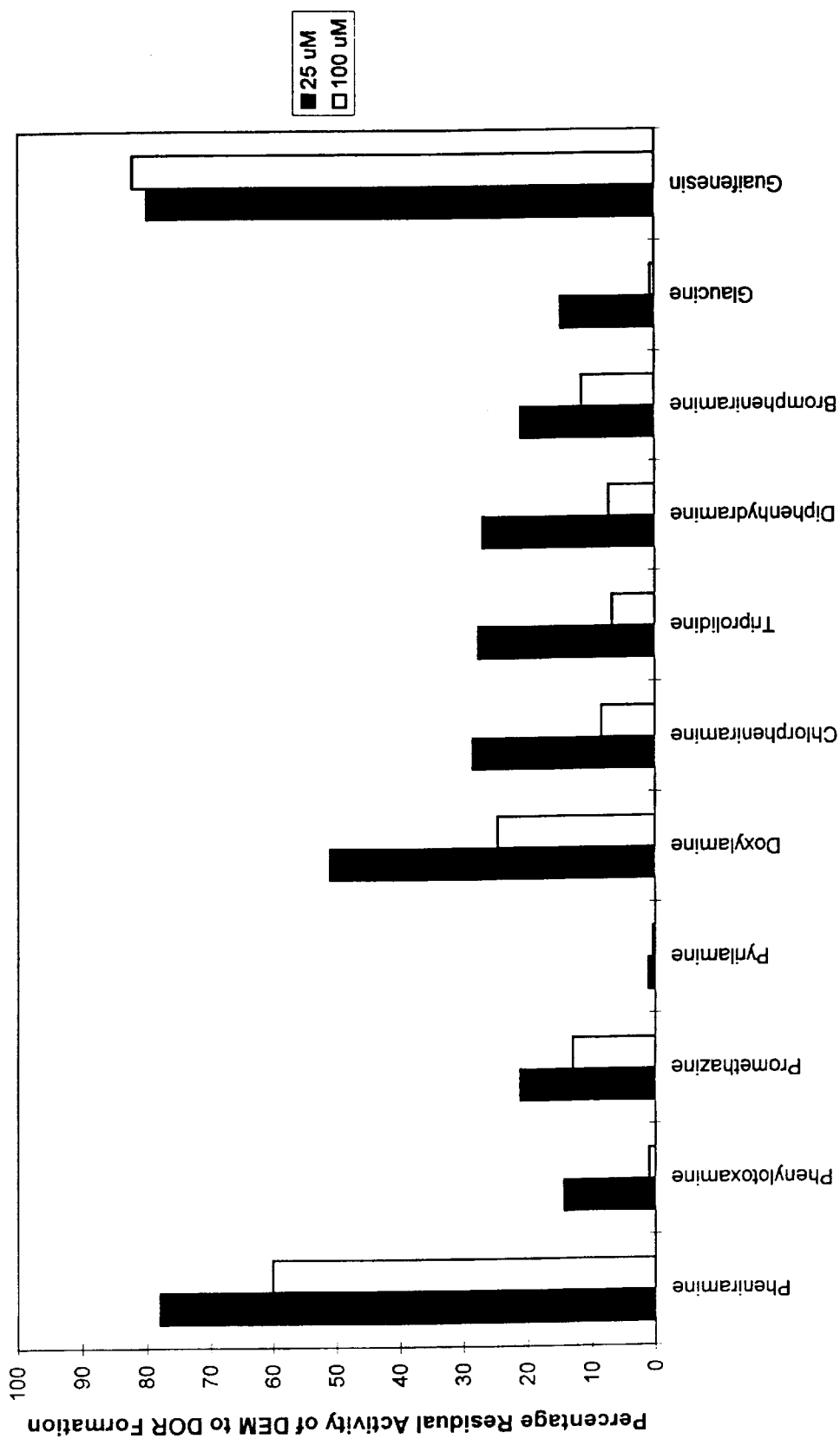
FIG. 3 is a histogram which shows inhibition of DEX to DOR metabolism by different compounds.
Figure 4A:
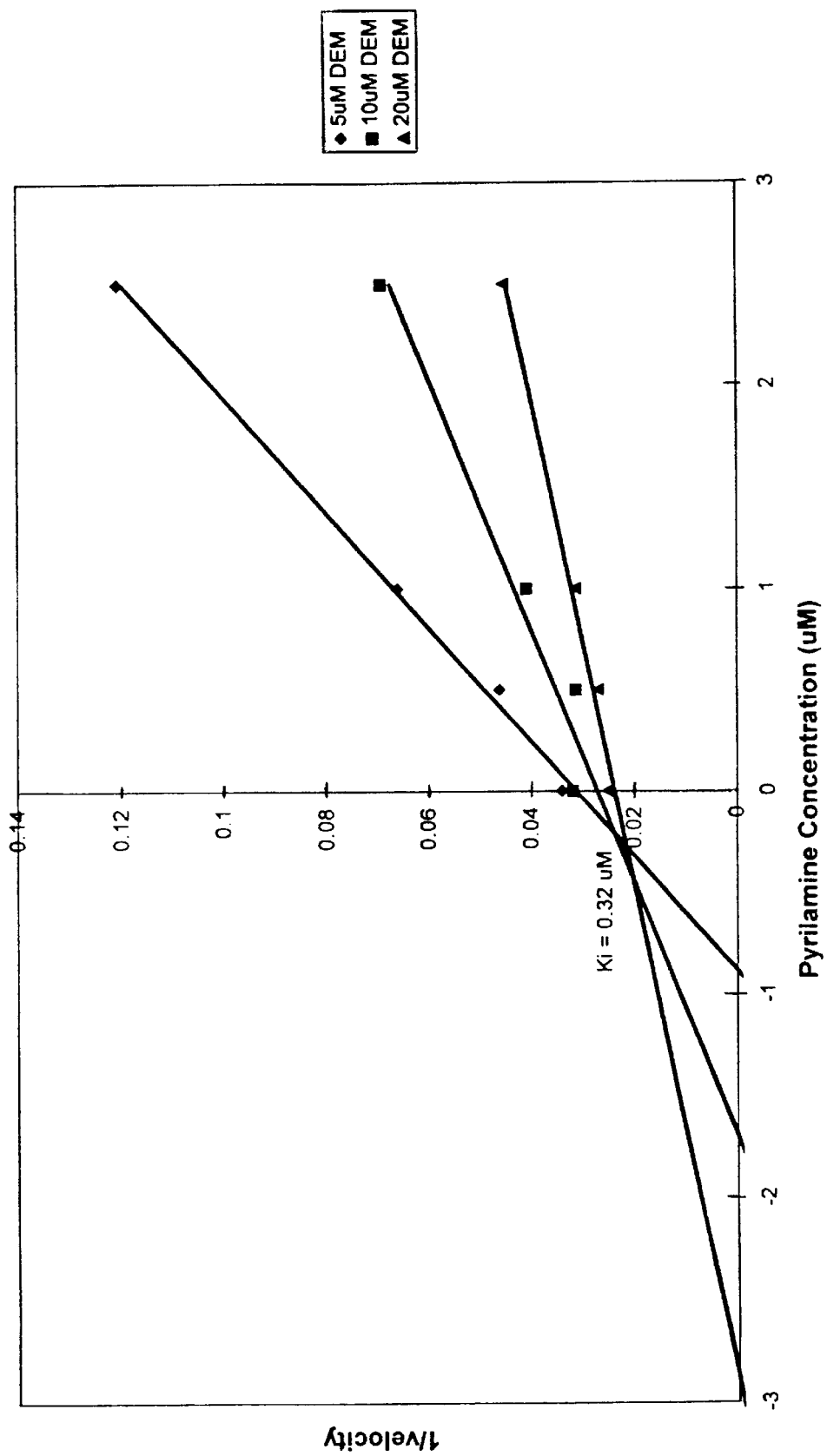
FIG. 4A is a graph showing Dixon plot of pyrilamine of DEM to DOR formation in K20 human liver microsome.
Figure 4B:
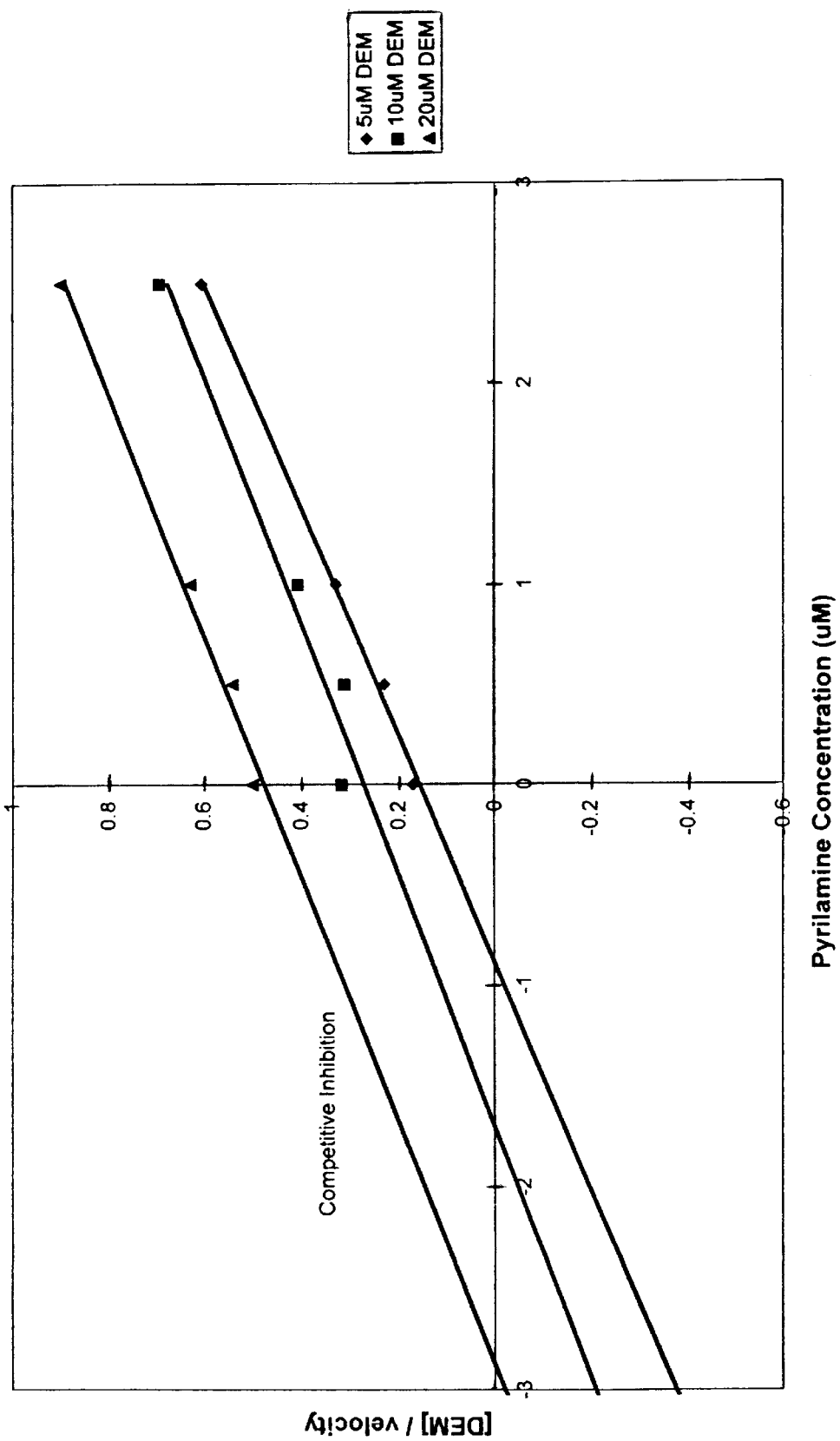
FIG. 4B is a graph showing Cornish-Bowden plot of pyrilamine inhibition of DEM to DOR formation in K20 human liver microsome.
Figure 5A:
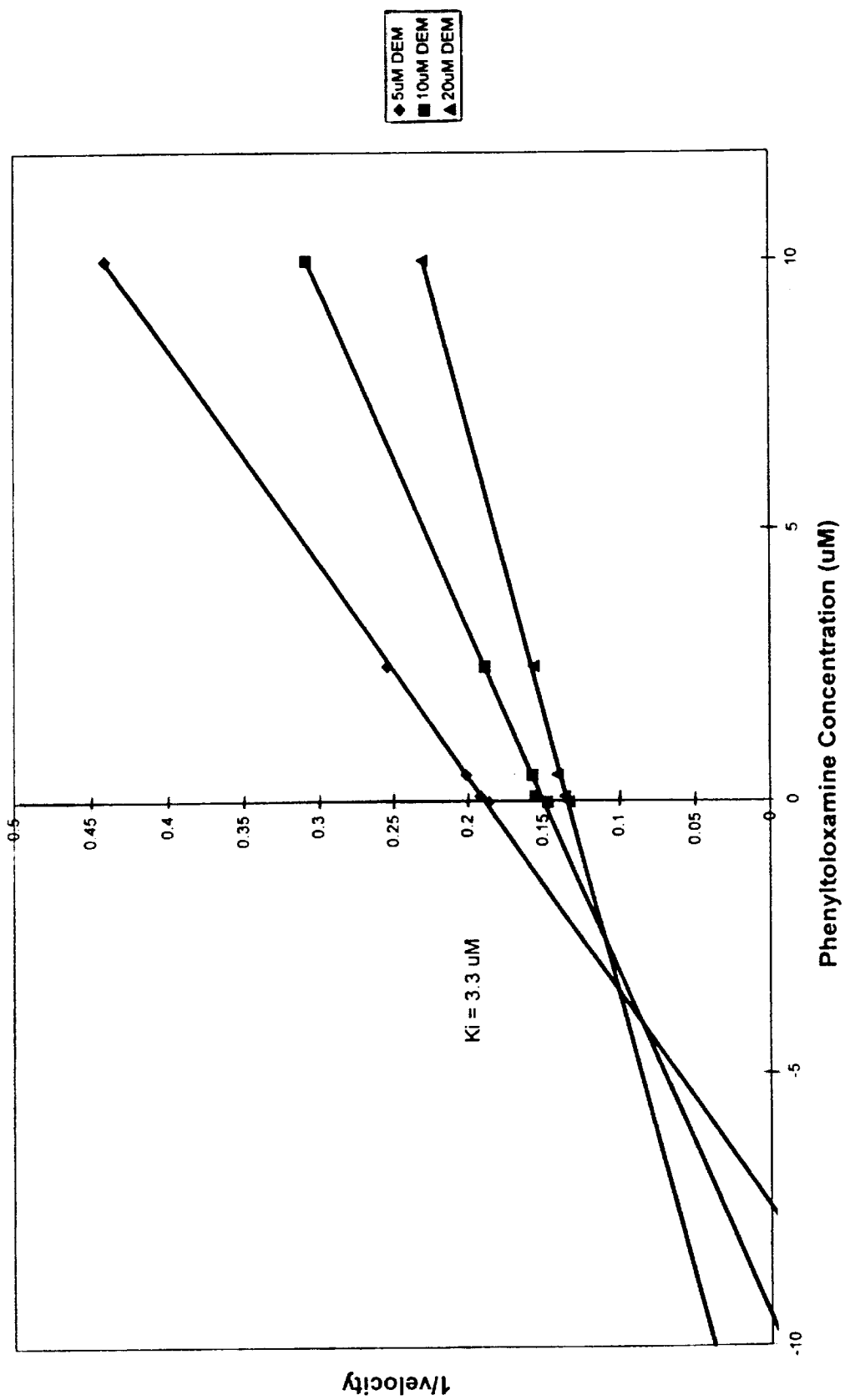
FIG. 5A is a graph showing Dixon plot of phenyltoloxamine inhibition of DEM to DOR formation in K20 human liver microsome.
Figure 5B:
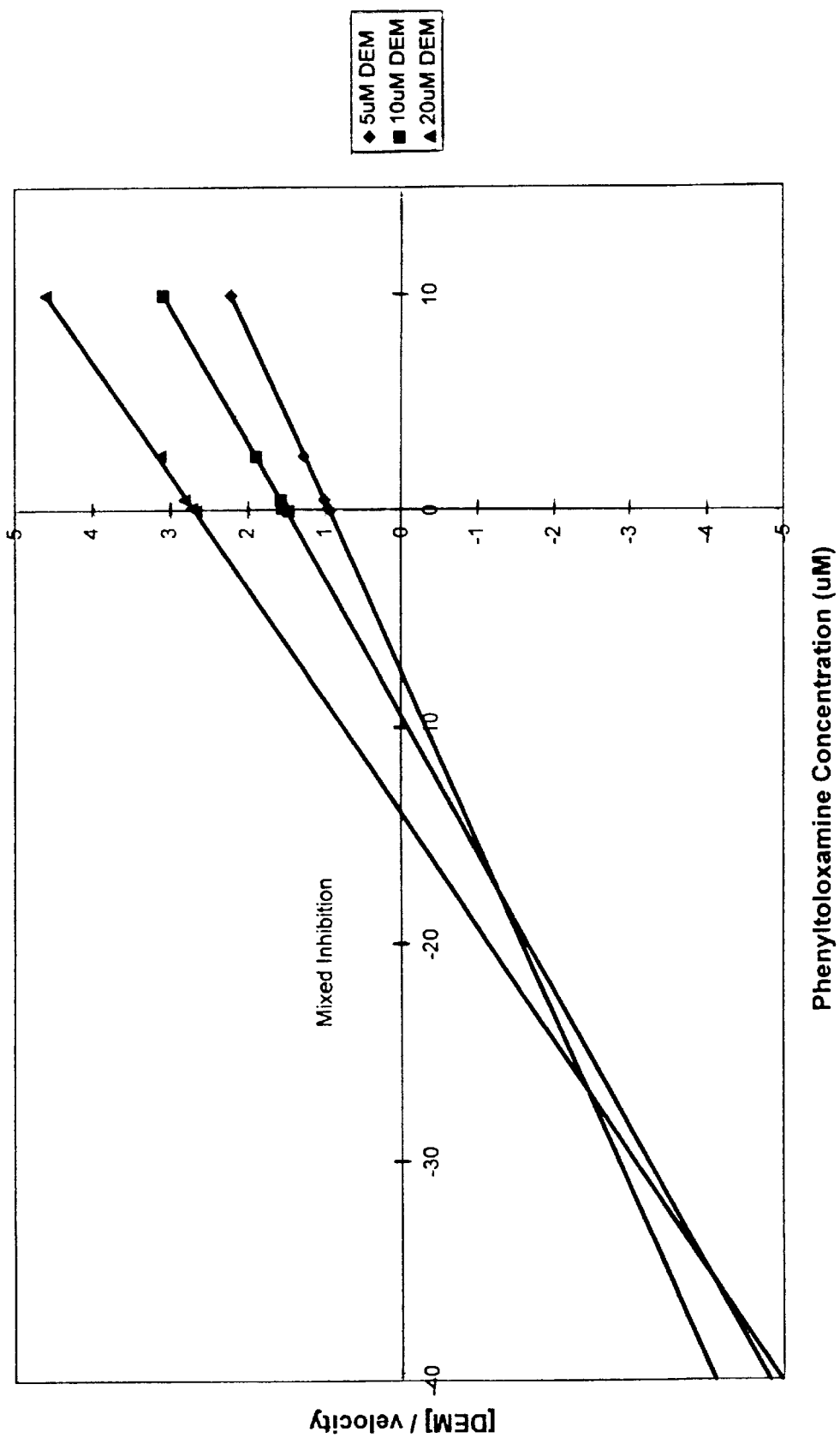
FIG. 5B is a graph showing Cornish-Bowden plot of phenyltoloxamine inhibition of DEM to DOR formation in K20 human liver microsome.
Figure 6A:
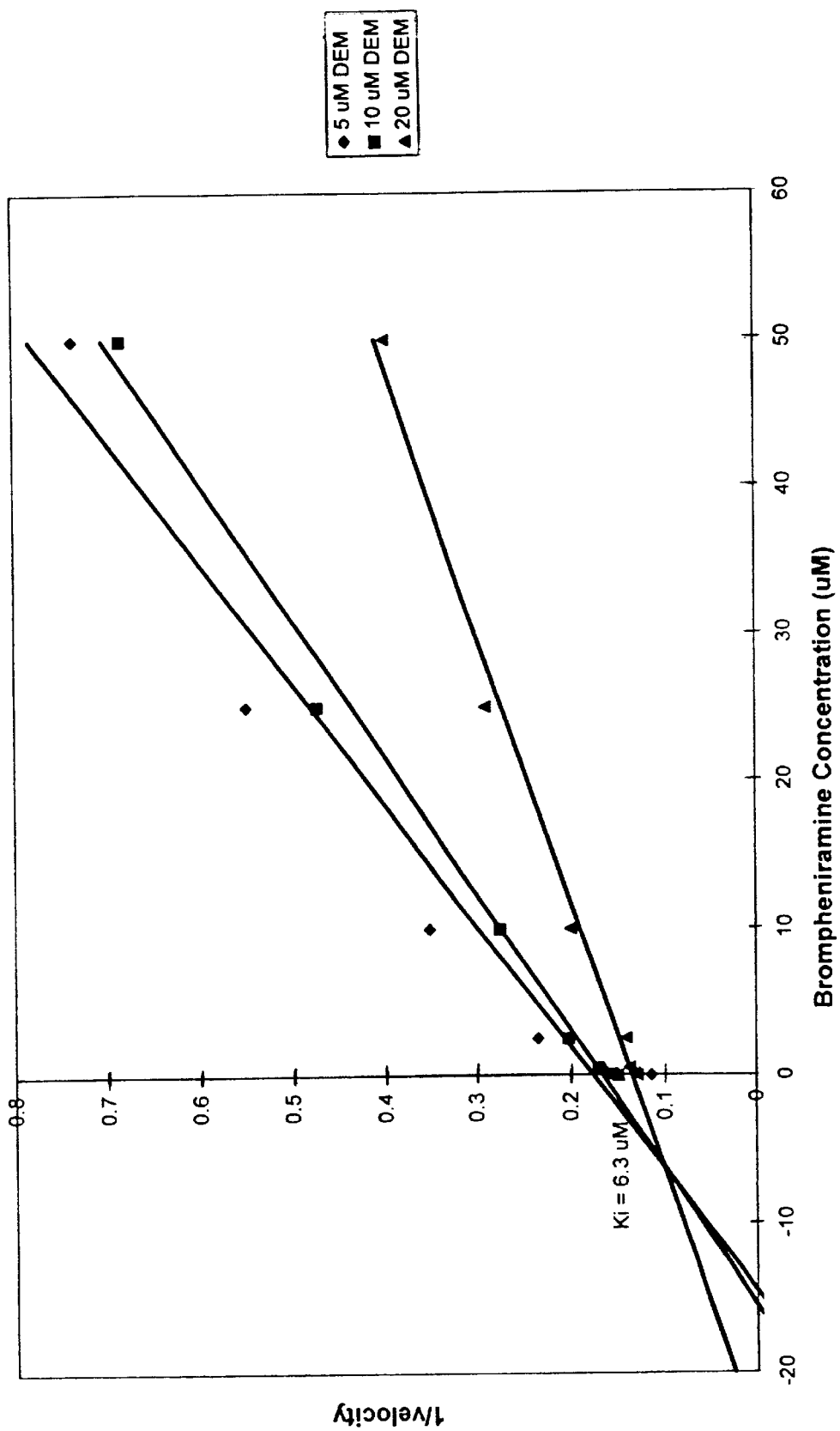
FIG. 6A is a graph showing Dixon plot of brompheniramine inhibition of DEM to DOR formation in K20 human liver microsome.
Figure 6B:
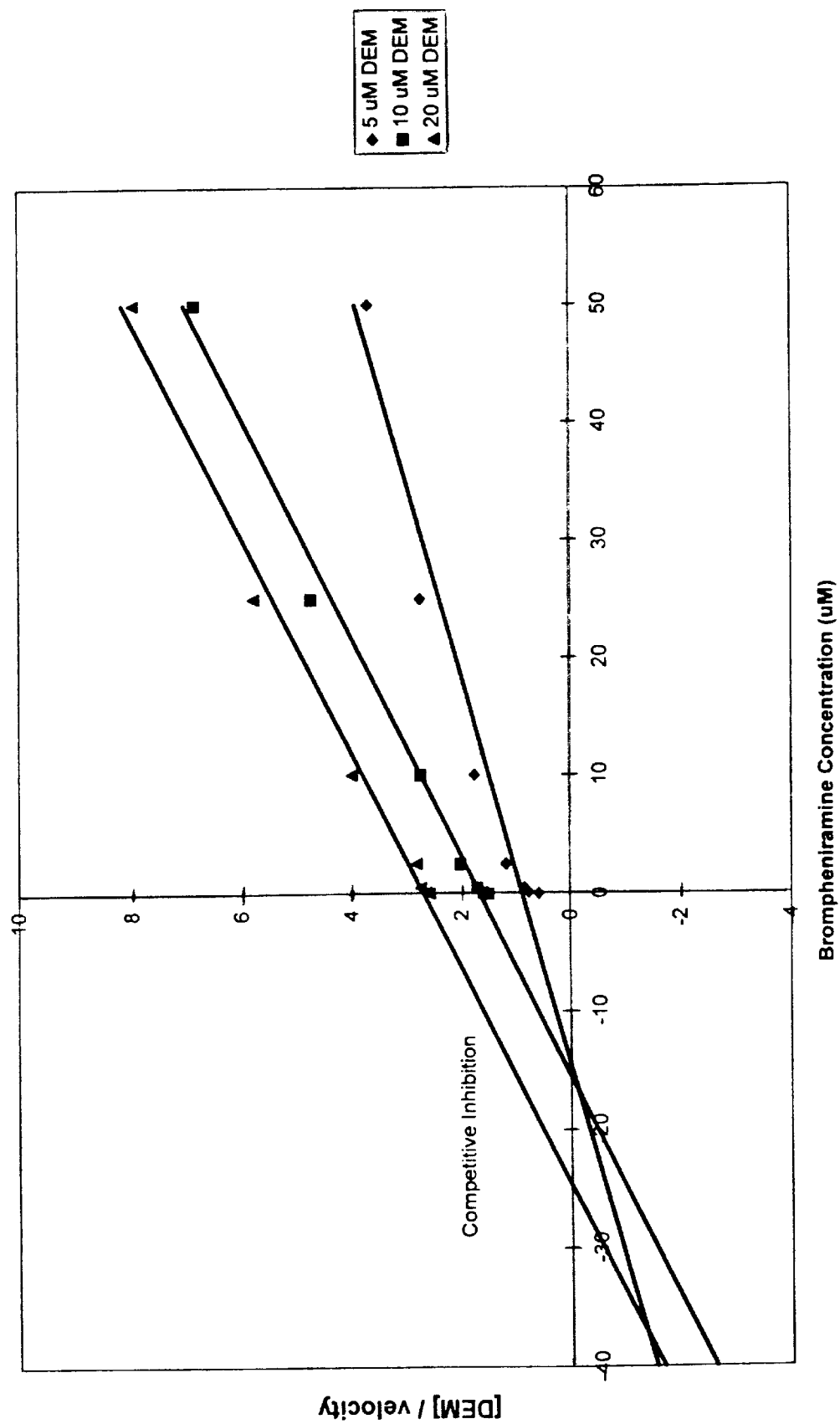
FIG. 6B is a graph showing Cornish-Bowden plot of brompheniramine inhibition of DEM to DOR formation in K20 human liver microsome.
Figure 7B:
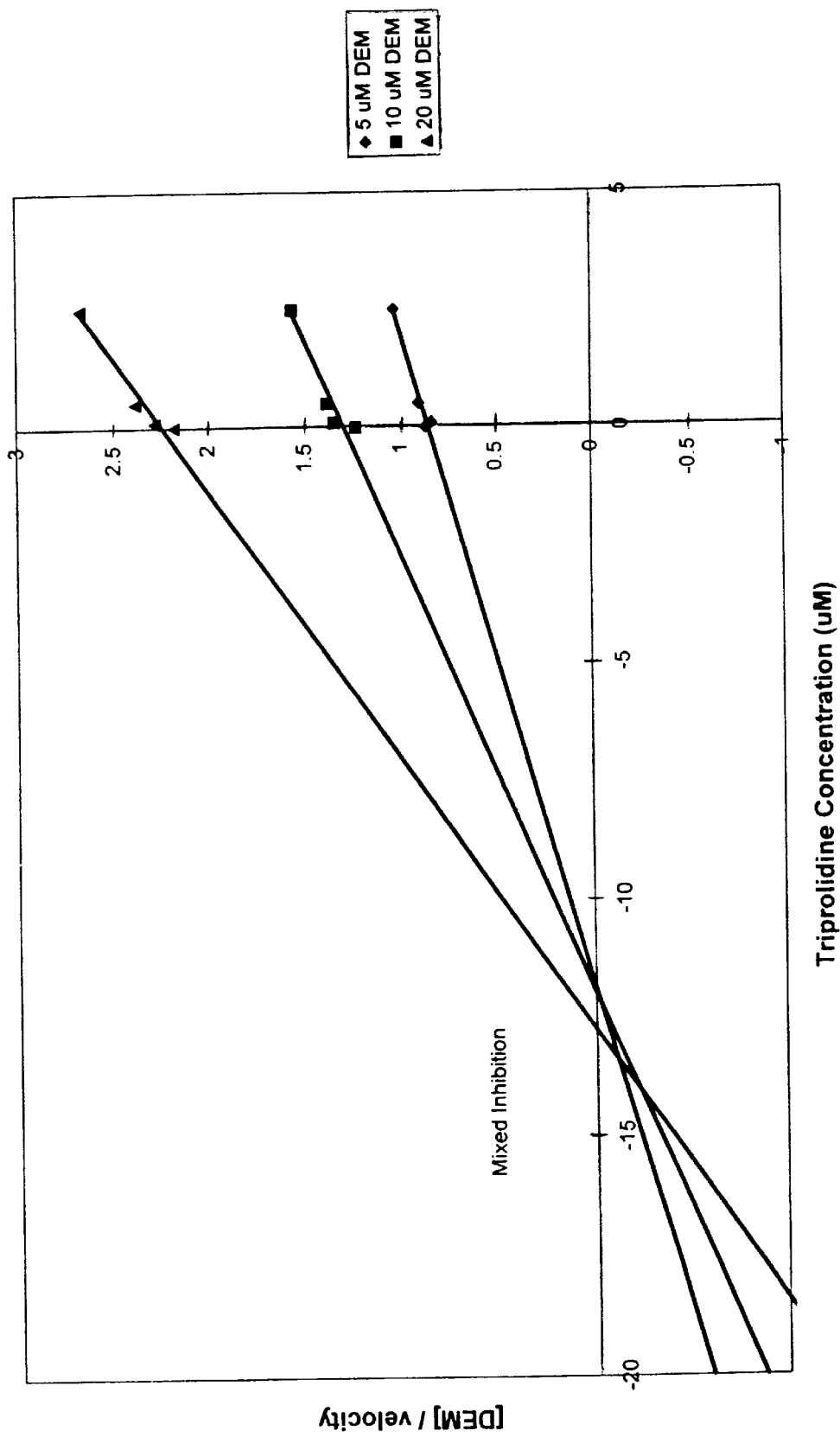
FIG. 7B is a graph showing Cornish-Bowden plot of triprolidine inhibition of DEM to DOR formation in K20 human liver microsome.
Figure 8A:
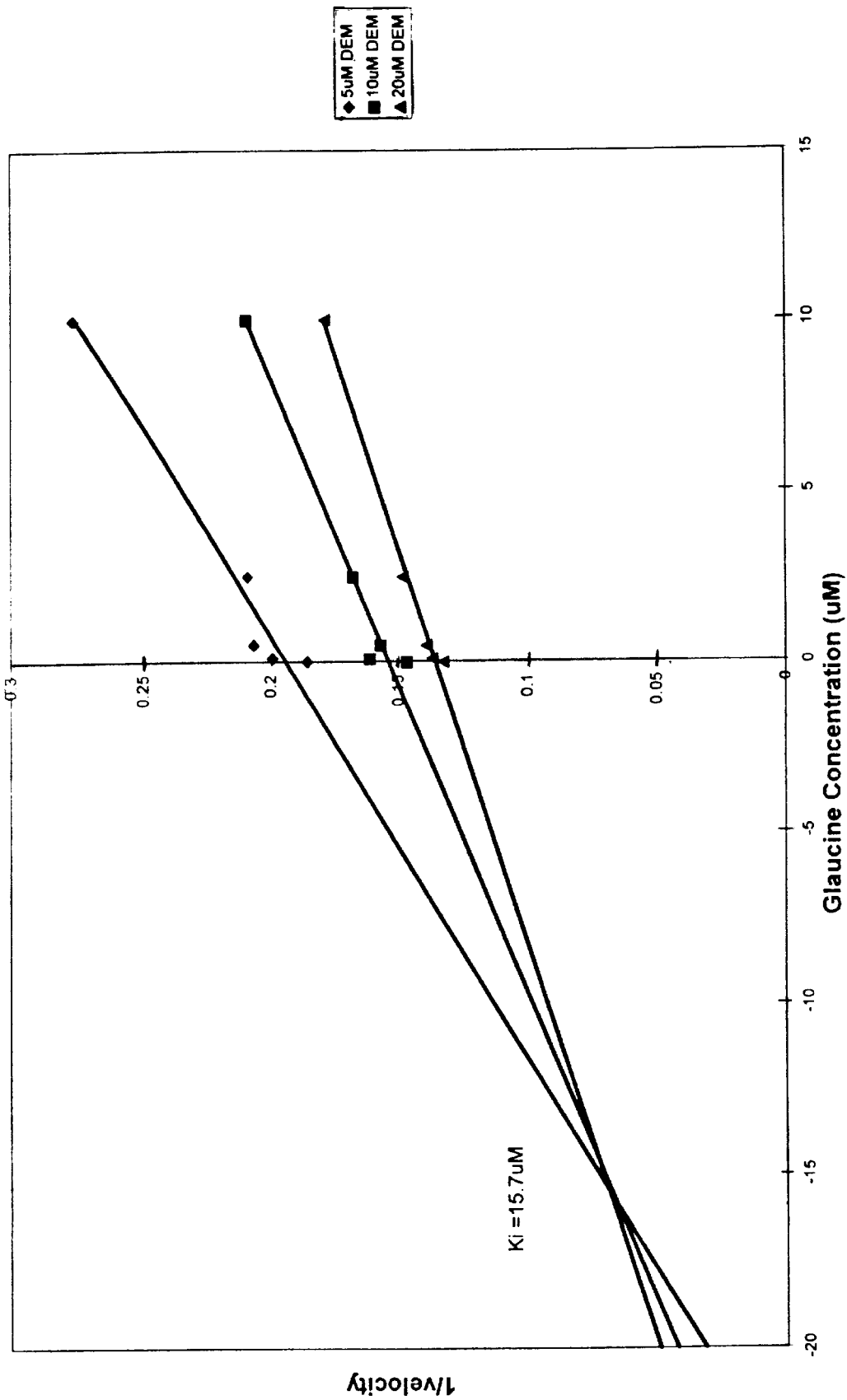
FIG. 8A is a graph showing Dixon plot of glaucine inhibition of DEM to DOR formation in K20 human liver microsome.
Figure 8B:
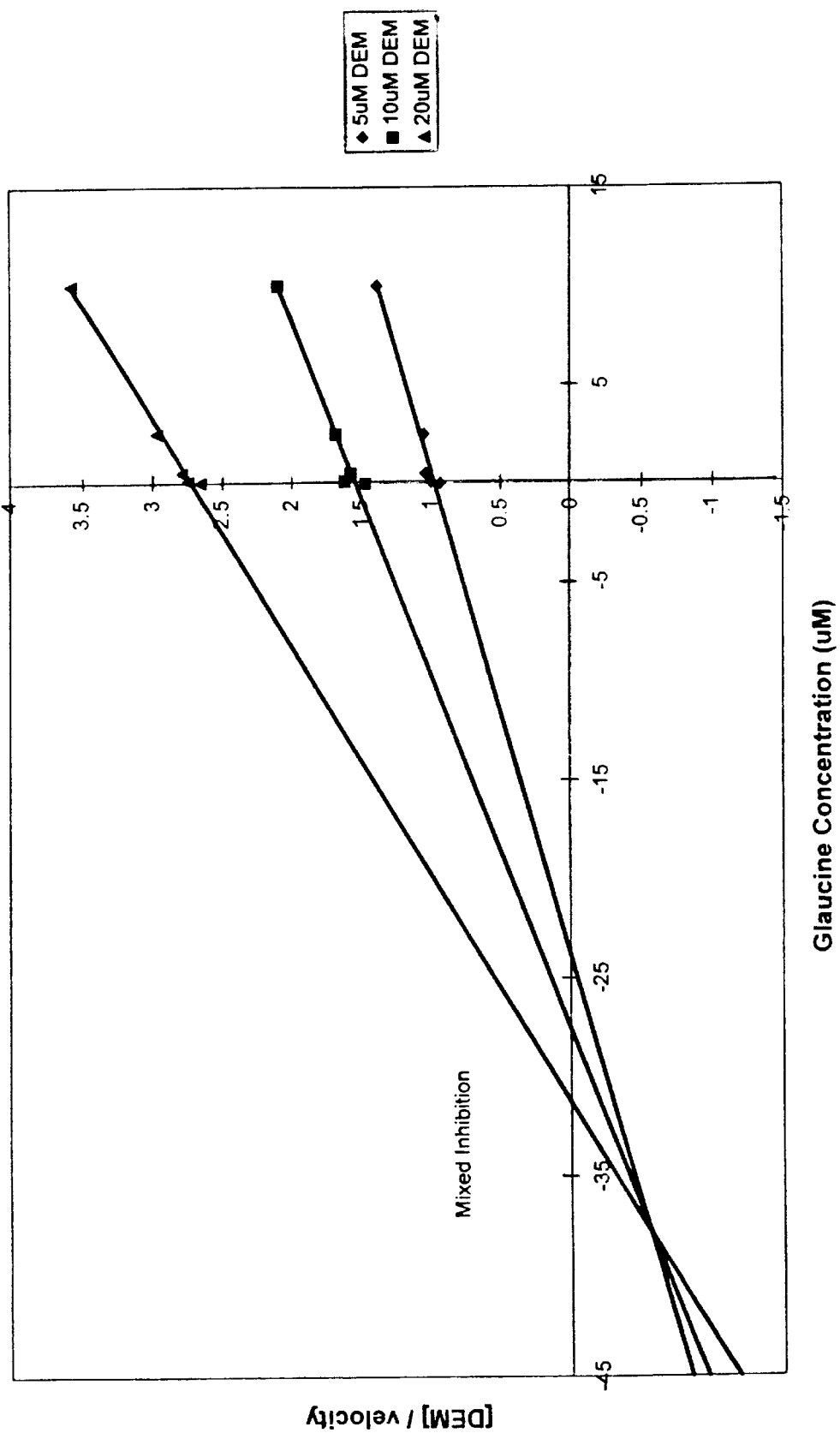
FIG. 8B is a graph showing Cornish-Bowden plot of glaucine inhibition of DEM to DOR formation in K20 human liver microsome.
Figure 9A:
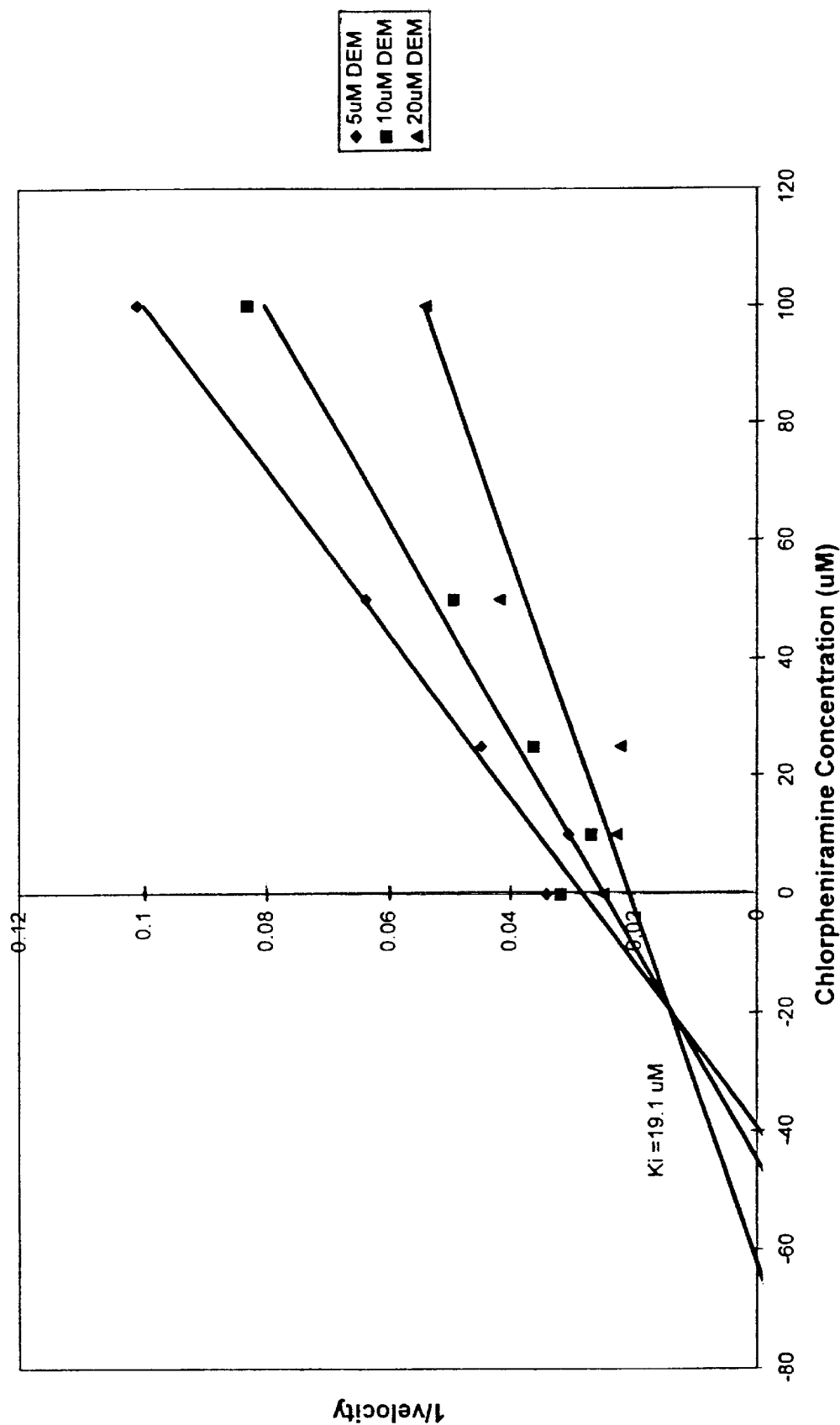
FIG. 9A is a graph showing Dixon plot of chlorpheniramine inhibition of DEM to DOR formation in K20 human liver microsome.
Figure 9B:
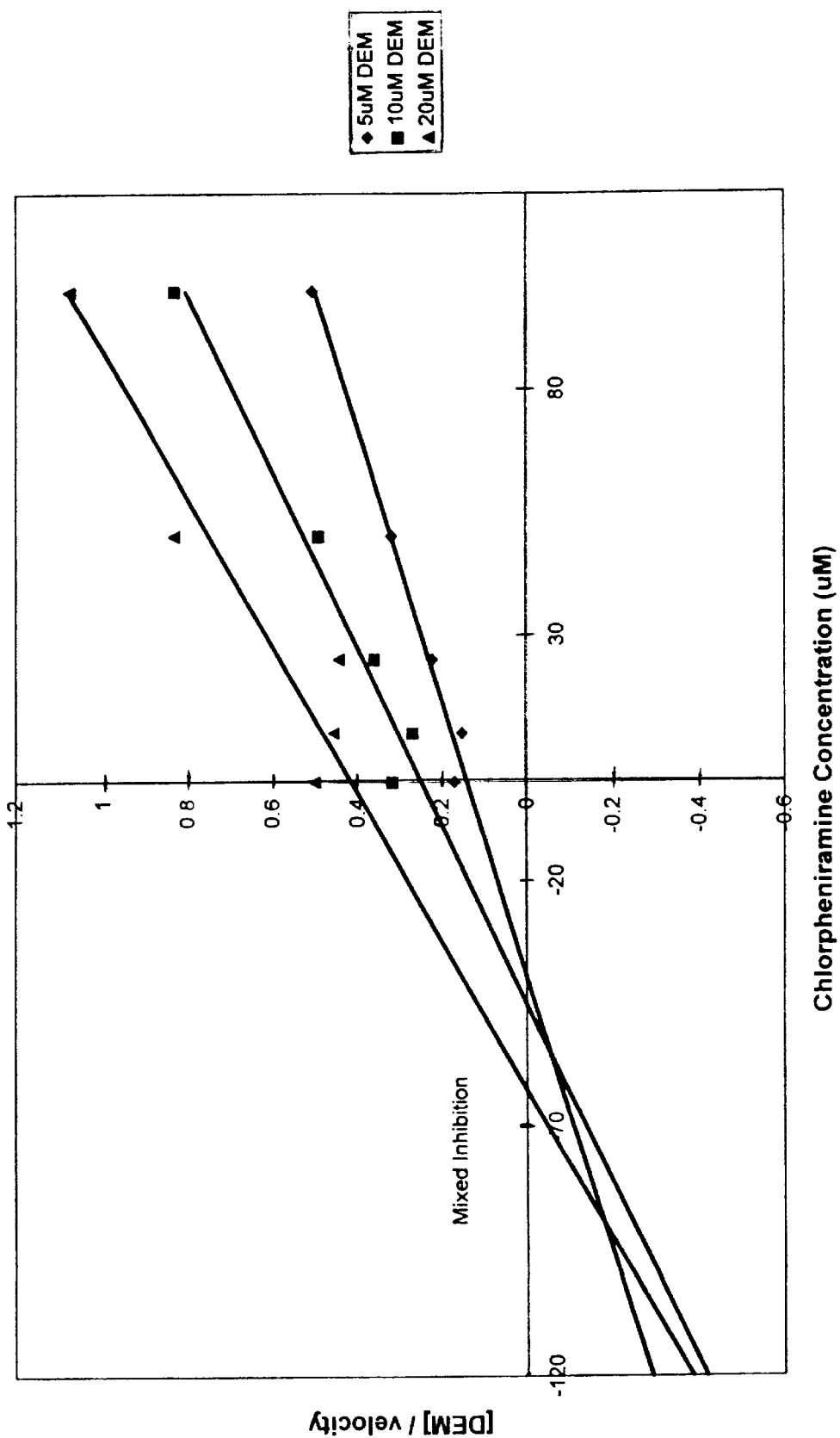
FIG. 9B is a graph showing Cornish-Bowden plot of chlorpheniramine inhibition of DEM to DOR formation in K20 human liver microsome.

A series of antihistamines and several components found in cough medications were initially screened for their inhibitory effect on CYP2D6 mediated DEM metabolism. The residual activity of CYP2D6 in the presence of the drug being investigated is shown in FIG. 3. Dixon Plots and Cornish-Bowen Plot (FIGS. 4A–9B) of the drugs, including pyrilamine, phenyltoloxamine, brompheniramine, triprolidine, glaucine and chlorpheniramine, which revealed strong inhibitory effect on DEM metabolism were generated. The same study was also performed for quinidine and quinine, which are antiarrthymic and antimalarial agents respectively, as a comparison. Table 1 presents the percentage inhibition, inhibition constants (Ki) and the type of the inhibition.

The rank order of potency based on the Ki values is:

Quinine>Pyrilamine>Phenylotoxamine>Brompheniramine>
Quinine>Triprolidine>Glaucine>Chlorpheniramine Enzyme Kinetics The rate of formation of the metabolite (nmoles of DOR/mg protein/min in CYP2D6) was plotted against DEM concentration and was fitted by the Michaelis-Menten equation using Enzfitter version 1.05. In Michaelis Menten kinetics, an enzyme-substrate complex is in dyanamic equilibrium with its components and forms reaction product at a rate proportional to the concentration of the complex (Endrenyi, L., 1989). The concentration of the substrate at which half of the enzyme become saturated is described as Km, or Michaelis constant. Vmax is the maximum velocity of the reaction in which all the enzymes are saturated (Cornish-Bowden, A., 1st ed., pp. 16–37).

Percentage Residual Activity

In the initial screening of the inhibitory effect of antihistamines and components found in cough medications on CYP2D6 mediated metabolism in human liver, the percentage residual activity of CYP2D6, which was the ratio of the amount of DOR produced in the presence of the drug being tested to that in the absence of the drug, was calculated. If a drug inhibited CYP2D6, the amount of DOR produced decreases since it is a metabolite of DEM via CYP2D6 pathway.

$$\text{Percentage Residue Activity}(\%) = \frac{\text{amount of } DOR \text{ produced in the presence of drug being tested}}{\text{amount of } DOR \text{ produced in the absence of drug being tested}} \times 100\%$$

Percentage Inhibition (%) = 100 − % residual activity

Dixon Plot & Cornish-Brown Plot

Dixon Plot is a graphical method used to quantitate the inhibitory effect of a drug. In this plot, the reciprocal of the velocity of the reaction (1/v) is plotted against the concentration of the inhibitor at two or more fixed concentrations of the substrate (Cornish-Bowden, A., 1st ed., pp. 16–37). In this experiment, the substrate used was DEM. The velocity of the reaction was reported as the concentration of DOR produced in nmoles/ml in the presence of 0.15 mg/ml of protein and incubated for 30 minutes.

Velocity=[DOR]nmoles/mg protein/min

From Dixon plot, the concentration of an inhibitor at which the straight lines produced from the set of points at each DEM concentration intersects in the upper left quandrant represents -Ki, which is the inhibition constant.

In order to distinguish whether a competitive inhibition, in which the apparent Km increases while Vmax remains the same, or a mixed-type inhibition, in which the apparent Km increases while Vmax decreases, is involved in the metabolism by an inhibitor, Cornish-Bowden plots were generated. In this method, the concentration of substrate divided by the velocity of the reaction ([DEM]/velocity) was plotted against the concentration of the inhibitor. If the set of straight lines at each level of substrate generated are parallel to each other, a competitive inhibition is revealed. If those set of straight lines converge in the lower left quandrant of the plot, a mixed-type inhibition is involved (Cornish-Bowden, A., 1st ed. pp. 73–96).

The results are shown in Table 1. They demonstrate that some antihistamines and glaucine the antitussive agent are potent inhibitors of the enzyme CYP2D6. A histogram presentation of the results of Table 1 may be seen in FIG. 2.

EXAMPLE 2

Antisense Inhibition Of CYP Genes

Another approach to inhibiting the activity of the CYP2D6 enzyme is to prepare an antisense sequence to the CYP2D6 gene. The preliminary results described below demonstrate that antisense techniques will be useful in inhibiting the activity of the CYP2D6 enzyme in human and animal models.

Antisense Approaches

It has been demonstrated that the ability to design antisense oligodeoxynucleotide (AS) knockdowns for specific members of supergene families, like the CYP supergene family. Specifically, using AS and missense oligodeoxynucleotides (MS) to the β3 subunit of the GABA$_A$ receptor supergene family in human HEK293 cell lines, we have shown a decrease in the β3 subunit. In collaboration with an electrophysiologist, Dr. Tim Hales of UCLA, the inventors have shown that administration of AS, but not MS or vehicle (VH), resulted in decreased chloride flux through the GABA$_A$ channel and a decrease in β3 receptor immunoreactivity (Davies et al., 1996). This suggests that AS can be used as a selective and effective approach for removing/decreasing particular members of the CYP family. This is invaluable, as selective chemical inhibitors of CYP sometimes have pharmacological actions, complicating behavioural studies; they may not be isozyme selective. AS are also valuable tools as novel pharmacological agents, particularly useful if a reversible inhibition is desired. The effectiveness of the antisense in specifically knowledge down CYP2D1 suggests that homologous knockouts will also be a possibly therapeutic in the future.

Cell Culture

It has been demonstrated the presence of CYP2D1, CYP2E1 and CYP2B1/2 mRNA and immunoreactivity in the rat hepatic (Fao) immortalized cell lines (Table 2A and 2B). Table 2A provides a summary of Immunocytochemistry results for 3 cell lines, namely rat hepatic fao cells; rat glioma C6 cells; and B65 neuroblastoma cells. Immunocytochemistry was performed using antibodies to three CYP families (anti-CYP2D, -CYP2E and -CYP2B). Table 2B provides a summary of mRNA results for 3 cell lines: 1) the rat hepatic fao cells; 2) the rat glioma C6 cells; and 3) B65 neuroblastoma cells. RT-PCR was performed using isozyme specific primers to three CYPs, CYP2D1, CYP2D4, CYP2E1, CYP2B1 and CYP2B2. These cell lines provide a system for testing the efficacy and selectivity of the AS to be used in vivo.

Antisense Design

Figure 10:
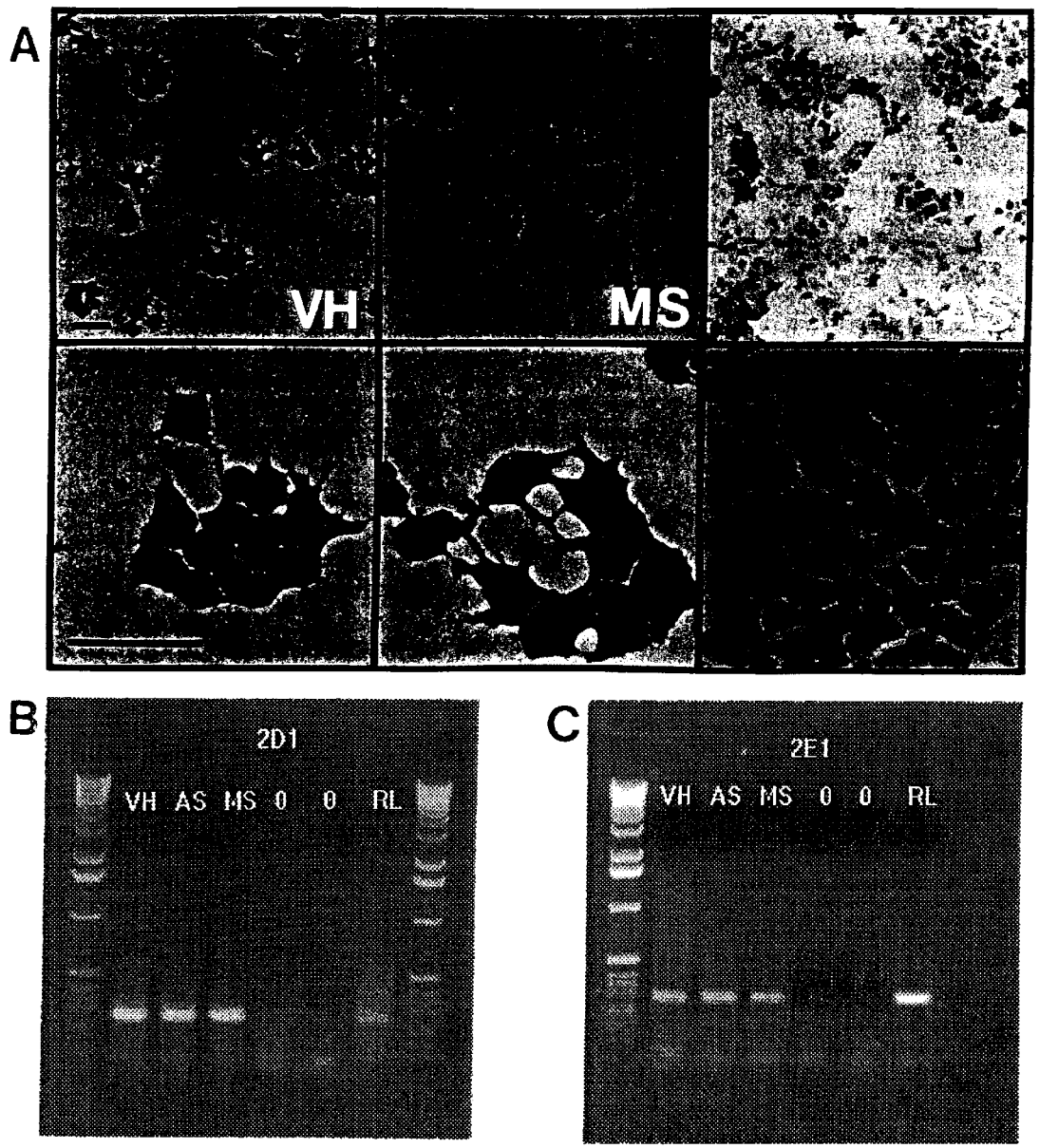
FIG. 10A is a photograph of rat hepatic cells cultured in the presence of vehicle (VH), missense (MS) and antisense (AS) and immunostained with a CYP2D6 antibody.
FIG. 10B shows the PCR results showing the mRNA production for the cells described in FIG. 10A.
FIG. 10C shows PCR results showing the control mRNA production for the cells described in FIG. 10A.

Initially the present inventors designed AS and MS primers to hybridize just 5' of the AUG translation start site. This may be seen at Table 2C which is a summary of the CYP2D family sequences near to the ATG. The ATG is shaded, as is the sequence where the antisense is designed. Nucleotides which are distinct from the CYP2D1 sequence in this region are also highlighted. FIG. 10C also shows the coding sequence, the antisense sequence used in the preliminary studies and the missense sequence, with the 2 pairs of nucleotides shaded which were switched to form the missense from the antisense. this common approach allows the AS to work either by RNAse H activity (destroying the doublestranded RNA/DNA hybrid), or by steric blockade of the translation start site. Sense OL can bind to genomic DNA and cause non-specific effects therefore, two pairs of nucleotides were switched to create MS, conserving nucleotide and chemical properties (Table 2C). As can be seen in Table 2C, the initial set of primers do not have sequence homology with other known genes (GenBank and the present inventors' own CYP database and do not self-anneal at body temperature. While the present inventors' goal is to decrease the CYP2D1 isozyme alone, we may remove both CYP2D1 and CYP2D5, due to their high degree of sequence homology. Little is known about CYP2D5 function in liver or brain; it may never be translated (Matsunaga et al., 1990).

with AS, while no decrease was seen in the Fao cell treated with MS when compared to VH control (FIG. 10A). These results demonstrate the antisense molecular techniques will be useful in knocking down the activity of CYP2D1/6 in animal models and in humans. This suggests that antisense technology is a viable alternative to chemical inhibitors for the elimination/diminishment of CYP2D1/6 enzymatic activity.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Inhibition of histamine H1 antagonists and glaucine on CYP2D6 mediated DEM metabolism

| Inhibitor | Pharmacological Action | [Inhibitor] | % Inhibition (DEM = 5 $\mu$M) | Apparent Ki | Type of Inhibition C = Competitive M = Mixed |
|---|---|---|---|---|---|
| Quinidine | Antiarrthymic Agent | 50 nM 200 $\mu$M | 30.9 61.4 | 74 nM | C |
| Pyrilamine | Antihistamine | 25 $\mu$M 100 $\mu$M | 61.4 99.7 | 0.32 $\mu$M | C |
| Phenyltoloxamine | Antihistamine | 25 $\mu$M 100 $\mu$M | 85.7 99.0 | 3.3 $\mu$M | M |
| Brompheniramine | Antihistamine | 25 $\mu$M 100 $\mu$M | 79.2 88.6 | 6.3 $\mu$M | C |
| Quinine | Antimalarial Agent | 5 $\mu$M 25 $\mu$M | 25.8 65.3 | 7.5 $\mu$M | C |
| Triprolidine | Antihistamine | 25 $\mu$M 100 $\mu$M | 72.6 93.3 | 10.1 $\mu$M | M |
| Glaucine | Antitussive Agent | 25 $\mu$M 100 $\mu$M | 85.4 99.3 | 15.7 $\mu$M | M |
| Chlorpheniramine | Antihistamine | 25 $\mu$M 100 $\mu$M | 71.7 91.6 | 19.1 $\mu$M | M |

The present inventors' goal in designing these primers, was 1) CYP2D1–5 specificity, followed by 2) CYP2D1 specificity.

CYP2D1 Antisense In Cultured Cells

Preliminary studies used the Fao rat hepatic line to determine OL efficacy. We have tested this using the normal phosphate backbone OL, with both AS and MS. Fao rat hepatic cell lines were grown in 50% confluency and treated for 24 h with lipofectin (120 $\mu$g/ml). Following treatment, these cells were fixed and stained with ICC using an anti-CYP2D1-human peptide antibody. These cells may be seen in FIG. 10A. Cells from duplicate plates to those used for ICC were harvested and subjected to RT-PCR using primers to CYP2D1 and CYP2E1 (RL=rate liver mRNA). A profound decrease in CYP2D immunoreactivity is seen only with the AS OL, while no change in CYP2D1 or CYP2E1 (control) mRNA was observed with any treatment. This may be seen in FIGS. 10B and 10C where the bar=100 $\mu$. This suggests that the ASL-OL is blocking translation of CYP2D1, but having no effect on CYP2D1 mRNA. In the result, the preliminary results demonstrate a profound disease in CYP2D1-immunoreactivity in the Fao cells treated

TABLE 2A

| | CELL LINES | | |
|---|---|---|---|
| ANTIBODY | FAO (hepatic) | C6 (glioma) | B65 (neuroblastoma) |
| anti-CYP2D6 | ++ | +++ | ++ |
| anti-CYP2E1 | NT | ++ | +++ |
| anti-CYP2B1 | NT | ++ | +++ |

NT: not tested

TABLE 2B

| | CELL LINES | | |
|---|---|---|---|
| mRNAs | FAO | C6 | B65 |
| CYP2D1 | +++ | ++ | ++ |
| CYP2D4 | + | ++ | ++ |
| CYP2E1 | +++ | + | + |

TABLE 2B-continued

| mRNAs | CELL LINES | | |
|---|---|---|---|
| | FAO | C6 | B65 |
| CYP2B1 | +++ | ++ | + |
| CYP2B2 | +++ | − | − |

TABLE 2C

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| CYP2D1 | A | G | C | C | T | G | G | C | A | G | C | A | G | C | A | A | G | G | C | A | G | C | C | C | A | G | G | A G C |
| CYP2D2 | A | A | G | C | C | T | G | C | A | A | G | C | C | G | T | C | G | G | C | A | G | C | C | A | T | G | G | G G C |
| CYP2D3 | A | G | C | C | T | G | G | C | A | G | C | A | G | C | G | G | G | G | C | A | G | A | C | A | T | G | G | A G C |
| CYP2D4 | A | A | C | C | C | A | A | A | C | A | G | C | A | G | C | A | G | G | C | A | G | C | C | A | T | C | A | G G A |
| CYP2D5 | A | G | C | C | T | G | G | C | A | G | C | A | G | C | A | G | G | G | C | A | G | T | C | A | T | G | G | A G C |

| | | | | | | | | | | | | | | | | | | | |
|---|---|---|---|---|---|---|---|---|---|---|---|---|---|---|---|---|---|---|---|
| CYP2D1 gene | 5'-T | G | G | G | C | A | G | C | A | G | C | A | A | G | G | C | A | G | -3' |
| Antisense OL | 5'-C | T | G | C | C | T | T | G | C | T | G | C | T | G | C | C | C | A | -3' |
| Missense OL | 5'-C | C | C | C | C | T | T | G | C | T | G | C | T | G | C | T | G | A | -3' |

REFERENCES

Alvan G, Bechtel P, Iselius L, Gundert-Remy U. Hydroxylation polymorphisms of debrisoquine and mephenytoin in European populations. *Eur J Clin Pharmacol* 1990: 39, 533–537.

Amir T. Personality study of alcohol, heroin, and poly-drug abusers in an Arabian gulf population. *Psychol Reports* 1994: 74, 515–520.

Baum C, Kennedy D L, Knapp D E, Faich G A, Anello C. Drug utilization in the U.S.—1986. In: U.S. Food and Drug Administration 8. Rockville, Md., 1987.

Beaver W T, Stanley L, Wallenstein S L, Houde R W. Analgesic studies of codeine and oxycodone in patients with cancer. II. Comparisons of intramuscular oxycodone with intramuscular morphine and codeine. *J Pharmacol Exp Ther* 1978: 207, 101–108.

Beck, A. T., Beamesderfer, A. Assessment of depression: The depression inventory, in Modern Problems in Pharmacopsychiatry. Edited by Pichot P. Basel, Krager, pp. 151–169, 1974.

Benowitz N L, Jacob P, Perez-Stable E. CYP2D6 phenotype and the metabolism of nicotine and cotinine. *Pharmacogenetics* 1996: 6, 239–242.

Bern, J. L. and Peck R. Dextromethorphan: an overview of safety issues. Durg Saf. 7:190–9, 1992.

Blin O., Azulay, J. P., Desneulle, C., Bille-Turo, F., Braguer, D., Besse, D., Branger, E., Crevat, A., Serratrice, G., Pouget, J. Y. A controlled one-year trial of dextromethorphan in amyotrophic lateral sclerosis. Clin. Neuropharmacol. 19:189–92, 1996.

Broly F, Gaedigk A, Heim M, Eichelbaum M, Morike K, Meyer U A. Debrisoquine/sparteine hydroxylation genotype and phenotype: Analysis of common mutations and alleles of CYP2D6 in a European population. *DNA Cell Biol* 1991:10, 545–558.

Brown, J., Kranzler, H. R., del Boca, F. K. Self-reports by alcohol and drug abuse in patients: Factors affecting reliability and validity. Br. J. Addict. 87:1013–1024, 1992.

Busto, U. E., Kaplan, H. L., Zawertailo, L., Sellers, E. M.: Pharmacologic effects and abuse liability of bretazenil, diazepam, and alprazolam in humans. Clin Pharmacol. Ther. 55: 451–463, 1994.

Caraco, Y., Sheller, J. and Wood, A. J. J. Pharmacogenetic determination of the effects of codeine and prediction of drug interactions. J. Pharmacol. Exp. Ther. 278(3): 1165–1174, 1996.

Caraco, Y., Sheller, J. and Wood, A. J. J. Pharmacogenetic determinants of doeine induction by rifampin: The impact of codeine's respiratory, psychomotor and miotic effects. J. Pharmacol. Exp. Ther. 281(1):330–336, 1997.

Chen Z. R., Somogyi A A, Bochner F. Polymorphic O-demethylation of codeine. *Lancet*, 1988: 2, 914–915.

Chen Z. R., Somogyi A A, Bochner F. Simultaneous determination of dextromethorphan and three metabolites in plasma and urine using high-performance liquid chromatography with application to their disposition in man. *Ther Drug Monit* 1990: 12, 97–104.

Chen, Z. R., Irvine, R. J., Bochner, F., Somogyi, A. A.: Morphine formation from codeine in rat brain; a possible mechanism of codeine analgesia. Life Sci. 46: 1067–1074, 1990.

Chen, Z. R., Irvine, R. J., Somogyi, A. A., Bochner, F.: Mu receptor binding of some commonly used opioids and their metabolites. Life Sci. 48: 2165–2171, 1991.

Cholerton S, Boustead C, Taber H, Arpanahi A, Idle J R. CYP2D6 genotypes in cigarettes smokers and non-tobacco users. *Pharmacogenetics* 1996: 6, 261–263.

Cole, J. O., Orzack M. H., Beake, B., Bird, M., Bar-Tal, Y.: Assessment of abuse liability of buspirone in recreational sedative users. J. Clin. Psychiatry 43: 69–75, 1982.

Cone, E. J., Darwin, W. D., W. D., Gorodetzky, C. W. and Tan, T.: Comparative metabolism of hydrocodone in man, rat, guinea pig, rabbit and dog. Drug Metab. Dispos. 6: 488–493; 1978.

Cornish-Bowden A. Introduction to enzyme Kinetics. In Fundamentals of Enzyme Kinetics (Cornish-Bowden A., 1st ed.). Butterworth, London. pp. 16–37.

Cornish-Bowden A. Introduction and activators. In Fundamentals of Enzyme Kinetics (Cornish-Bowden A., 1st ed.). Butterworth, London. pp. 73–96.

Daly A R, Brockmöller J, Broly F, Eichelbaum M, Evans W E, Gonzalez F J, Huang J-D, Idle J R, Ingelman-Sundberg M, Ishizaki T, Jacqz-Aigrain, Meyer U A, Nebert D W, Steen V M, Wolf C R, Zanger U M. Nomenclature for human CYP2D6 alleles. *Pharmacogenetics* 1996: 6, 193–201.

Davies, P. A., Hoffman, E., Carlisle, H. J., Tyndale, R. F., Hales, T. G. Do GABAA receitprs in WSS-1 cells use an HEK-293 beta3 subunit? Society for Neurosciences, 1996.

Davis H, Baum C, Graham D J. Indices of drug misused for prescription drugs. *Int J Addict* 1991: 26, 777–795.

Dayer, P., Desmeulesm J., Leemann, T., Stiberni, R.: Bioactivation of the narcotic drug codeine in human liver is mediated by the polymorphic monoxygenase catalyzing debrisoquine 4-hydroxylation (ctyochrome P-450 dbl/bufl). Biochem. Biophys. Res. Commun. 152: 411–416, 1988.

de Morais S M F, Wilkenson G R, Balaisdell, J, Nakamura K, Meyer U A, Goldstein J A. The major genetic defect responsible for the polymorphism of S-mephenytoin metabolism in humans. *J Biol Chem* 1994: 269, 15419–15422.

Desmeules, J., Gascon, M-P., Dayer, P., Magistris, M.: Impact of environmental and genetic factors on codeine analgesia. Eur. J. Clin. Pharmacol. 41: 23–26, 1991.

Diagnostic and Statistical Manual of Mental Disorders, Fourth Edition (DSM-IV). American Psychiatric Association, Washington, 1994.

Di Chiara, G. and North, A.: Neurobiology of opiate abuse. Trends Pharmacol. Sci. 13: 185–193, 1992.

Endrenyi, L., Dose Response Relationship. In Principles of Medical Pharmacology (Kalant H and Roschlau W, 5th ed.). B.C. Decker Inc., Toronto. pp. 77–83; 1989.

Fernandez-Salguero P, Hoffman S M, Cholerton S, Mohrenweisser, H, Raunio H, Rautio A, Pelkonen O, Huang J D, Evans W F, Idle J R, Gonzalez F J. A genetic polymorphism in coumarin 7-hydroxylation: sequence of the human CYP2D6 genes and identification of variant CYP2D6 alleles. *Am J Hum Genet* 1995: 57, 651–660.

Fischman, M. W., Foltin, R. W: General methods of drug abuse liability assessment: Utility of subjective-effects measurements in assessing abuse liability of drugs in humans. Br. J. Addict. 86: 1563–1570, 1991.

Flammang A M, Gelboin H V, Aoyama T, Gonzalez F J, McCoy G D. Nicotine metabolism by cDNA-expressed human cytochrome P450s. *Biochem Arch* 1992: 8, 1–8.

Geter-Douglass, B., Witkin, J. M. Discriminative stimulus effects of low affinity uncompetitive NMDA antagonists. NIDA Res. Monograph. 162:356, 1996.

Gorski J. C., Jones, D. R., Wrighton, S. A., Hall, S. D. Characterization of dextromethorphan N-demethylation by human liver microsomes: contribution of the cytochrome P450 3A (CYP3A) subfamily. Biochem. Pharmacol. 48:173–82, 1994.

Hampton, R. Y., Medzihradsky, F., Woods, J. H., Dahlstrom, P. J. Stereospecific binding of $^3$H-phencyclidine in brain membranes. Life Sci. 30:2147–54, 1982.

Health & Welfare Canada. Narcotic, controlled and restricted drug statistics—Analysis report. Health and Welfare Canada, Ottawa, 1991: 21, 33, 41–48, 53.

Heim, M. H. and Meyer, U. A.: Genotyping of poor metabolizers of debrisoquine by allele-specific PCR amplification. Lancet 336: 529–532, 1990.

Heim, M. H., Meyer, U A. Evolution of a highly polymorphic human cytochrome P450 gene cluster: CYP2D6. *Genomics* 1992: 14, 49–58.

Hennies, J. J., Friderichs, F. and Schneider, J.: Receptor binding, analgesic and antitussive potency of tramadol and other selected opioids. Arzneim. Forsch. Drug Res. 38: 877–880, 1988.

Herheimer A. *Dug and Therapeutics Bulletin* 23(16): 62–64, 1985.

Himmelsbach, C. K., Andrews, J. H., Felic, R. H., Oberst, F. W., Davenport, L. F.: Studies on codeine addiction. Publ. Hlth. Rep. 158: 1–67, 1940.

Hollander, D., Pradas J., Kaplan, R., McLeod, H. L. Evans, W. E., Munsat, T. L. High-dose dextromethorphan in amyotrophic lateral sclerosis: phase I safety and pharmacokinetic studies. Ann. Neurol. 36:920–4, 1994.

Holtzman S. G. Phencyclidine-like discriminative effects of opioids in the rat. J. Pharmacol. Exp. Ther. 214:614–9, 1980.

Issac, P., Seto, W., Lanctot, K. L., Busto, U. E.: Use and abuse of prescription opioids in Canada 1978 to 1989. Can. J. Clin. Pharmacol. 2(2): 81–86, 1995.

Jacqz-Agrain E., Funck-Brentano, C., Cresteil, T. CYP2D6 - and CYP3A-dependent metabolism of dextromethorphan in humans. Pharmacogenetics 3:197–204, 1993.

Jaffe, J. H., Martin W. R., Goodman and Gilman's the Pharmacological Basis of Therapeutics (Gilman A. G., Nies A. S., Taylor P., 8th ed.), Pergamon Press, New York, pp. 485–521.

Jasinski, D. R.: Assessment of the abuse potential of morphine-like drugs (methods used in man). In Handbook of Experimental Pharmacology, Volume 45/1. Drug Addiction J: Morphine, Sedative Hypnotic and Alcohol Dependence. Ed. By: W. R. Martin, pp. 197–258, Springer-Verlag, Heidelberg, 1977.

Jensen, S. and Hansen, A. C.: Abuse of codeine separated from over-the-counter drugs containing acetylsalicylic acid and codeine. Int. J. Leg. Med. 105:279–282, 1993.

Johanson, C. E., Uhlenhuth, E. H.: Drug self-administration in humans. In: Self-Administration of Abused Substances: Methods for Study No. 20, ed. by N. A. Krasnegor, pp. 68–85, US Government Printing Office, Washington, 1980.

Kaplan, H. L.: Representation of on-line questionnaires in an editable, auditable database. Behav. Res. Methods Instruments Comput. 24: 373–384, 1992.

Kaplan, H. L.: Rapid computerized determination of pupil diameter from imperfect video images. Problems of Drug Dependence, 1994 Proceedings of the 56th Annual scientific Meeting, The College on Problems of Drug Dependence, Inc. NIDA Research Monograph 153, p. 436. National Institute on Drug Abuse, Rockville, Md., 1995.

Kaplan, H. L.: SMS: A software strategy for acute effects studies. Problems of Drug Dependence, 1995: Proceedings of the 57th Annual scientific Meeting, The College on Problems of Drug Dependence, Inc. NIDA Research Monograph 162, p. 188. National Institute on Drug Abuse, Rockville, Md., 1996.

Kaplan, H. L., Busto, U. E., Baylon, G. J., Cheung, S. W., Otton, S. V., Somer, G. and Sellers, E. M. Inhibition of cytochrome P450 2D6 metabolism of hydrocodone to hydromorphone does not importantly affect abuse liability. J. Pharmacol. Exp. Ther. in press.

Kathiramalainathan, K., Kaplan, H. L., Busto, U. E., Romach, M. K., Tyndale, R. F., Sellers, E. M. Inhibition of cytochrome P450 2D6 modifies codeine metabolism and abuse liability. Abstracts of XIth International Symposium on Microsomes and Drug Oxidations (Los Angeles, Calif.), 239, 1996.

Kauppila T., Gronroos, M., Perlovaara, A. An attempt to attenuate experimental pain in human dextromethorphan, an NMDA receptor antagonist. Pharmacol. Biochem. Behav., 52:641–4, 1995.

Kay, D. C., Gorodetzky, C. W., Martin, W. R.: Comparative effects of codeine and morphine in man. J. Pharmacol. Exp. Ther. 156(1): 101–106, 1967.

Kodaira, H. and Spector, S. Transformation of thebaine to oripavine, codeine, and morphine by rat liver, kidney, and brain microsomes. Proc. Natl. Acad. Sci. 85: 1267–1271, 1988.

Korkok M. Canadian government study shows big rise in Canadian use of several narcotics. Can Med Assoc J 1979: 120, 1270–1271.

Koyuncuoglu H., Sadam B. The treatment of heroin addicts with dextromethorphan: a double-blind comparison of dextromethorphan with chlorpromazine. Int. J. Clin. Pharmacol. Ther. Toxicol. 28:147–52, 1990.

Kroemer, H. K., Eichelbaum, M.: "It's the genes, stupid": Molecular bases and clinical consequences of genetic cytochrome P450 2D6 polymorphism. Life. Sci. 56(26): 2285–2298, 1995.

Martin, W. R., Sloan, J. W., Sapira, J. D. and Jasinski, D. R. Physiologic, subjective, and behavioral effects of amphetamine, methamphetamine, ephedrine, phenmetrazine and methylphenidate in man. Clin. Pharmacol. Ther. 12: 245–258, 1971.

Martin, W. R., Sloan, J. W., Shapiro, J. D. and Jasinski, D. R.: Physiologic, subjective, and behavioral effects of amphetamine, methamphetamine, ephedrine, phenmetrazine and methylphenidate in man. Clin. Pharmacol. Ther. 12: 245–258, 1971.

Matsunaga E., Umeno M., Gonzalez F. The rat P450 IID subfamily: complete sequence of four closely linked genes and evidence the gene conversions maintained sequence homologeity at the heme-binding region of the cytochrome P450 active site. J. Mol. Evol. 1990; 30:155–169.

Microsoft Exel [lsqb] computer program [rsqb]. Version 5.0c. Microsoft Corporation, Trade Secret, Soft-Art, Inc. Seattle, Wash. Copyright 1984–94.

Montastruc, J. L., Fabre, N., Rascol, O., Senard, J. M. N-methyl-D-aspartate (NMDA) antagonism and Parkinson's disease: a pilot study with dextromethorphan. Mov. Disord. 9:242–3, 1994.

Mortimer, O., Persson, K., Ladona, M. G., Sparding, D., Zanger, U. M., Meyer, U. A., Rane, A.: Polymorphic formation of morphine from codeine in poor and extensive metabolizers of dextromethorphan: Relationship to the presence of immunoidentified cytochrome P-450IID1. Clin. Pharmaco.l Ther. 47: 27–35, 1990.

Newman, A. H., Shah, J. H., Izenwasser, S., Heller, B., Mattson, M. V., Tortella, F. C. Highly selective sigma 1 ligands based on dextromethorphan. Med. Chem. Res. 6:102–17, 1996.

O'Brien, C. P. Drug addiction and drug abuse: In: Hardman J, Limbird L, eds. Goodman and Gilman's The Pharmacological Basis of Therapeutics. 9th edition. Toronto: MacGraw-Hill, 1996: 557–577.

O'Conner L E, Berry J W, Morrison A, Brown S. The drug of choice phenomenon: psychological differences among drug users who preferred different drugs. Inter J Addict 1995: 30, 541–555.

Otton S V, Schadel M, Cheung S W, Kaplan H L, Busto U F, Sellers E M, CYP2D6 phenotype determines the metabolic conversion of hydrocodone to hydromorphone. Clin Pharmacol Ther 1993a: 54, 463–472.

Otton, S V, Wu D, Joffe R T, Cheung S W, Sellers E M. Inhibition by fluoxitine of cytochrome P450 2D6 activity. Clin Pharmacol Ther 1993b: 53, 401–409.

Parsons, C. G., Quanck, G., Bresink, I., Baran, L., Przegalinski, E., Kostowski, W., Krzascik, P., Harmann, S., Danysz, W. Comparison of the potency, kinetics, and voltage-dependency of a series of incompetitive NMDA receptor antagonists in vivo with anticonvulsive and motor impairment activity in vivo. Neuropharmacology 34:1239–58, 1995.

Pollack, B., Drug Info. J. 1996; 30:669–74.

Poulsen, L., Brøsen, K., Arendt-Nielson, L., Gram, L. F., Elbrek, K. and Sindrup, S. H. Codeine and morphine in extensive and poor metabolizers of sparteine: Pharmacokinetics, analgesic effect and side effects. Eur. J. Clin. Pharmacol. 51:289–295, 1996.

Reisine T, Pasternak G. Opioid analgesics and antagonists. In: Hardman, J, Limbird L, eds. Goodman and Gilman's The Pharmacological Basis of Therapeutics. 9th edition. Toronto: MacGraw-Hill, 1996: 521–555.

Romach, M. K., Sproule, B. A., Sellers, E. M., Somer, G. and Busto, U. F.: Long-term codeine use is associated with depressive symptoms. Am. J. Psychiatry, 1997 (submitted).

Rosner B. Hypothesis testing: Categorical Data. In: Fundamentals of Biostatistics. 2nd edition. Boston: Duxbury Press, 1988: 302–367.

Rounsaville B J, Weissman M M, Kleber H D. The significance of alcoholism in treated opiate addicts. J Nerv Ment Dis 1982: 170, 479–488.

SAS Institute Inc.: SAS/STAT User's Guide, Release 6.03 Edition. SAS Institute Inc., Cary, N.C., 1990.

Saenz, R., Tanner, C. M., Albers, G., Kurth, M., Tetrud, J. A preliminary study of dextromethorphan (DM) as adjunctive therapy in Parkinson's disease (PD) [lsqb] abstract [rsqb]. Neurology, A155:15, 1993.

Schmid, B., Bircher, J., Preisig, R., Kupfer, A.: Polymorphic dextromethorphan metabolism: co-segregation of oxidative O-demethylation with debrisoquin hydoxylation. Clin. Pharmacol. Ther. 38: 618–24, 1985.

Seevers, M. H., Pfeiffer C. C.: A study of the analgesia, subjective depression, and euphoria produced by morphine, heroin, dilaudid and codeine in the normal human subject. J. Pharmacol. Exp. Ther. 56: 166–187, 1936.

Shadel, M., Wu, D., Otton, S. V., Kalow, W., Sellers, E. M. Pharmacokinetics of dextromethorphan and metabolites in humans: Influence of the CYP2D6 phenotype and quinidine inhibition. J. Clin. Psycopharmacol 15(5): 263–269, 1995.

Sindrup, S. H., Brosen, K., Bjerring, P., Arendt-Nielsen, L., Larsen, U., Angelo, H. R., Gram, L. F.: Codeiene increases pain thresholds to copper vapor laser stimuli in extensive but not poor metabolizers of sparteine. Clin. Pharmacol. Ther. 48: 686–693, 1990.

Sindrup, S. H., Arendt-Nielsen, L., Brosen, K., Bjerring, P., Angelo, H. R., Eriksen, B., Gram, L. F.: The effect of quinidine on the analgesic effect of codeine. Eur. J. Clin. Pharmacol. 42: 587–592, 1992.

Sindrup, S. H. and Brosen, K.: The pharmacogenetics of codeine hypoalgesia. Pharmacogenetics 5: 335–346, 1995.

Single, E., McKenzie D M. Canadian profile: alcohol and drug abuse. Toronto: Addiction Research Foundation, 1994.

Small L F, Eddy N B, Mosettig E, Himmelsbach C K. Studies on Drug Addiction, Suppl. 138. Washington: U.S. Government Printing Office, 1983.

Stillman, R., Petersen, R. C. The paradox of phencyclidine (PCP) abuse. Ann. Intern. Med. 90:428–9, 1979.

Svensson, J. O., Rane, A., Sawe, J., Sjoqvist, F.: Determination of morphine, morphine-3-glucuronide and (tentatively) morphine-6-glucuronide in plasma and urine using ion-pair high-performance liquid chromatography. J. Chromatogr. 230: 427–432, 1982.

Svensson, J. O.: Determination of morphine, morphine-6-glucuronide and normorphine in plasma and urine with high-performance liquid chromatography and electrochemical detection. J. Chromatogr. 375: 174–178, 1986.

Székely, J. L.: Opioid peptides in substance abuse. pp 1–14, 55–80, 235–250, 251–264, CRC Press Inc, Boca Raton, 1994.

Tortella, F. C., Pellicano, M., Bowery, N. G. Dextromethorphan and neuromodulation: old drug coughs up new activities. Trends Pharmacol. Sci. 10:501–7, 1989.

Tucker G T, Lennard M S, Ellis S W, Woods H F, Cho A K, Lin L Y, Hiratsuka A, Schitz D A, Chu T Y. The demethylation of methylenedioxymethamphetamine ("ecstasy") by debrisoquine hydoxylase (CYP2D6). *Biochem Pharmacol* 1994: 47, 1151–1156.

Tyndale, R. F., Droll, K. P., Sellers, E. M., Genetically deficient CYP2D6 metabolism provides protection against oral opiate dependence. *Pharmacogenetics* 1997, 7:375–379.

Tyndale, R. F., Rao, Y., Hoffman, E., Kwan, M. Expression of cytochromes P450 in cells derived from the Brain. International Soceity for the Study of Xenobiotics.

Tyndale, R. F., Sunahara, R., Inaba, T., Kalow, W., Gonzales F. J., Niznik H. B. Neuronal cytochrome P450IID1 (debrisoquine/sparteine-type): Potent inhibition of activity by (-)-cocaine and nucleotide sequence identify to human hepatic P450 gene CYP2D6. Mol. Pharmacol. 40: 63–68, 1991.

Uhl G R. Association strategies in substance abuse. In: Jansson B, Jornvall H, Rydberg V, eds. Toward a molecular basis of alcohol use and abuse. Basal: Birkhausen, 1994: 131–141.

Walker, F. O., Hunt, V. P. An open label trial of dextromethorphan in Huntington's disease. Clin Neuropharmacol. 12:322–30, 1989.

Wong, B. Y., Coulter, D. A., Choi, D. W., Prince, D. A. Dextrorphan and dextromethorphan, common antitussives, are antiepileptic and antagonize N-methyl-D-asparate in brain slices. Neurosci. Lett. 85:261–6, 1988.

Wu, D., Otton, S. V., Sproule, B. A., Busto, U., Inaba, T., Kalow, W. and Sellers, F. M. Inhibition of human cytochrome P450 2D6 (CYP2D6) by methadone. Br. J. clin. Pharmac. 35: 30–34, 1993.

Wu D, Otton S V, Inaba T, Kalow W, Sellers E M. Interactions of amphetamine analogs with human liver CYP2D6. *Biochem Pharmacol* 1996 (in press).

Yue, Q. Y., Svenson J-O., Alm, C., Sjoqvist, F., Sawe, J.: Interindividual and interethnic differences in the demethylation and glucuronidation of codeine. Br. J. Clin. Pharmacol. 128: 629–637, 1989.

Yue, Q. Y., Hasselstrom, J., Svensson, J. O., Sawe, J.: Pharmacokinetics of codeine and its metabolites in Caucasian healthy volunteers: Comparisons between extensive and poor hydroxylators of debrisoquine. Br. J. Clin. Pharmac. 31: 635–642, 1991.

Zawertailo, L. A., Busto, U., Kaplan, H. L., Sellers, E. M.: Comparative abuse liability of sertraline, alprazolam, and dextroamphetamine in humans. J. Clin. Pyschopharmacology 15(2): 117–124, 1995.

We claim:

1. A method for inhibiting the metabolism of a drug that is metabolized by the enzyme CYP2D6 to prolong the activity of the drug comprising administering an effective amount of at least one CYP2D6 inhibitor selected from the group consisting of glaucine, brompheniramine, promethazine pyrilamine, doxylamine, diphenhydramine, phenyltoloxamine, triprolodine and chloropheniramine to an animal in need thereof.

2. A method according to claim 1 wherein the effectiveness of the drug is increased as compared to the effectiveness of the drug in the absence of the inhibitor.

3. A method according to claim 1 wherein the abuse potential of the drug is decreased as compared to the abuse potential of the drug in the absence of the inhibitor.

4. A method according to claim 1 wherein the drug suppresses cough.

5. A method according to claim 4 wherein the drug is dextromethorphan.

6. A method according to claim 4 wherein the drug is codeine.

7. A long lasting and reduced abuse potential composition comprising (a) a drug that is metabolized by the enzyme CYP2D6, and (b) a CYP2D6 inhibitor selected from the group consisting of pyrilamine, brompheniramine, triprolodine, promethazine, doxylamine, diphenhydramine, chloropheniramine, and glaucine.

8. A composition according to claim 7 for the treatment of cough or colds comprising: (1) a drug that is effective in treating coughs or colds, and (2) a CYP2D6 inhibitor that inhibits the metabolism of the drug and is selected from the group consisting of pyrilamine, brompheniramine, triprolodine, promethazine, doxylamine, diphenhydramine, chloropheniramine, and glaucine.

9. A composition according to claim 8 wherein the drug is dextromethorphan.

10. A composition according to claim 8 wherein the drug is codeine.

11. A composition according to claim 8 comprising: (i) dextromethorphan, and (ii) glaucine.

12. A composition according to claim 8 comprising: (i) codeine, and (ii) glaucine.

* * * * *